(12) United States Patent
Son et al.

(10) Patent No.: US 12,377,061 B2
(45) Date of Patent: Aug. 5, 2025

(54) COMPOSITION FOR PROMOTING HAIR GROWTH COMPRISING A GUANINE DERIVATIVE

(71) Applicants: KOREA RESEARCH INSTITUTE OF BIOSCIENCE AND BIOTECHNOLOGY, Daejeon (KR); IMMUNOMET THERAPEUTICS INC., Houston, TX (US)

(72) Inventors: Myung Jin Son, Daejeon (KR); Kyung-Sook Chung, Daejeon (KR); Sung Wuk Kim, Seongnam-si (KR); Jiae Kook, Daejeon (KR); Hong Bum Lee, Daejeon (KR); Sanghee Yoo, Houston, TX (US); Youjeong Kwon, Daejeon (KR); Seonju Mun, Daejeon (KR); Jiwon Ahn, Daejeon (KR); Jae Sung Ryu, Daejeon (KR)

(73) Assignees: KOREA RESEARCH INSTITUTE OF BIOSCIENCE AND BIOTECHNOLOGY, Daejeon (KR); IMMUNOMET THERAPEUTICS INC., Houston, TX (US)

(*) Notice: Subject to any disclaimer, the term of this patent is extended or adjusted under 35 U.S.C. 154(b) by 669 days.

(21) Appl. No.: 17/293,595

(22) PCT Filed: Nov. 14, 2019

(86) PCT No.: PCT/KR2019/015572
§ 371 (c)(1),
(2) Date: May 13, 2021

(87) PCT Pub. No.: WO2020/101400
PCT Pub. Date: May 22, 2020

(65) Prior Publication Data
US 2022/0000811 A1    Jan. 6, 2022

(30) Foreign Application Priority Data
Nov. 14, 2018    (KR) .................. 10-2018-0139777

(51) Int. Cl.
*A61K 31/155*    (2006.01)
*A61G 7/00*    (2006.01)
(Continued)

(52) U.S. Cl.
CPC .............. *A61K 31/155* (2013.01); *A61G 7/00* (2013.01); *A61K 8/43* (2013.01); *A61P 17/14* (2018.01)

(58) Field of Classification Search
None
See application file for complete search history.

(56) References Cited

U.S. PATENT DOCUMENTS 4,596,812 A    6/1986    Chidsey, III et al.
2004/0258652 A1    12/2004    Pascaly et al.

FOREIGN PATENT DOCUMENTS

HU    0400762    11/2005
JP    06-056633    3/1994
(Continued)

OTHER PUBLICATIONS

Miranda et al., J Invest Dermatol. Apr. 2018;138(4):968-972 (Year: 2018).*
Dong et al. Progress on mitochondria and hair follicle development in androgenetic alopecia: relationships and therapeutic perspectives. Stem Cell Res Ther 16, 44 (2025) (Year: 2025).*
(Continued)

*Primary Examiner* — Jeffrey S Lundgren
*Assistant Examiner* — Anthony Joseph Seitz
(74) *Attorney, Agent, or Firm* — LEX IP MEISTER, PLLC

(57) ABSTRACT

The present invention relates to a composition for hair improvement, and more specifically to a composition for promoting hair growth, or preventing or treating hair loss,
(Continued)

comprising a guanine derivative having no toxicity as an active ingredient. The composition has excellent effects of promoting hair growth and regenerating hair follicles, and thus can be effectively used in various fields such as pharmaceutical, food, feed, and cosmetic compositions for promoting hair growth, or preventing, treating, and improving hair loss.

9 Claims, 26 Drawing Sheets

(51) Int. Cl.
  *A61K 8/43*    (2006.01)
  *A61P 17/14*    (2006.01)
  *A61Q 7/00*    (2006.01)

(56) References Cited

FOREIGN PATENT DOCUMENTS

| | | |
|---|---|---|
| JP | 2017-513948 | 6/2017 |
| KR | 10-2015-0022731 | 3/2015 |
| WO | WO-2015160220 A1 * 10/2015 | ............. A61K 31/36 |

OTHER PUBLICATIONS

EPO, a the extended European search report of application No. 19884438.3 dated Sep. 26, 2022.
Database GNPD [Online] Mintel, "Korres:Tonifying and Fortifying Shampoo for Men", Korres Natural Products (Jul. 14, 2016), http://www.gnpd.com.
Database GNPD [Online] Mintel, "Propoline: Tonic Hair Mask", Apivita (Dec. 5, 2001), http://www.gnpd.com.
Arise, K. et al, "Optimization of biguanide derivatives as selective antitumor agents blocking adaptive stress responses in the tumor microenvironment", Drug Design, Development and Therapy, 2014, 8, pp. 701-717.
Son, M. J. et al, "A novel and safe small molecule enhances hair follicle regeneration by facilitating metabolic reprogramming", Experimental & Molecular medicine, 2018, 50, pp. 1-15, Dec. 6, 2018.
Gwang Seong Choi, "Hair characteristics and androgenetic alopecia inKoreans", Journal of the Korean Medical Association, 56(1): 45-54.
Miranda, Matilde, et al. "Topical inhibition of the electron transport chain can stimulate the hair cycle." The Journal of investigative dermatology 138.4 (Apr. 2018): 968-972.
JPO, Office Action of the corresponding Japanese Patent Application No. 2021-526463 , dated Aug. 2, 2022.

* cited by examiner

[Fig. 1]
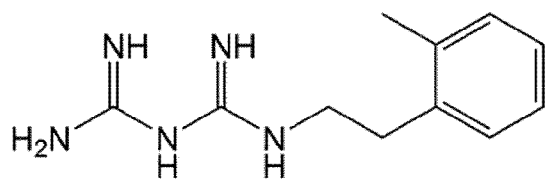 IM176OUT05 - IM
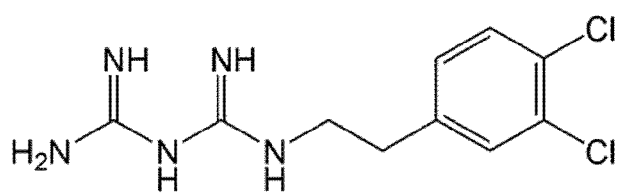 IM176OUT04
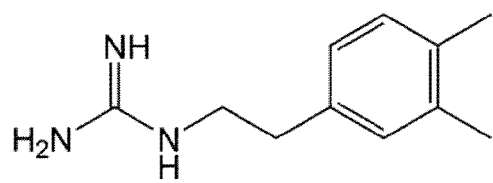 IM177OUT02
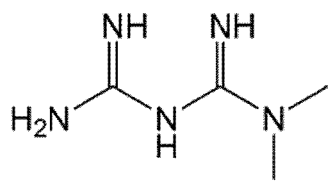 Metformin
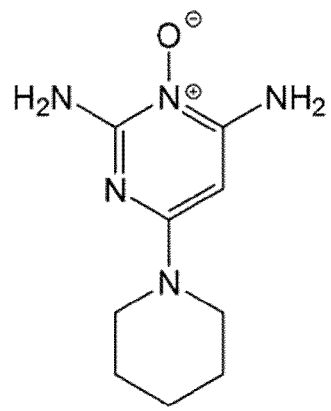 Minoxidil

[Fig. 2]
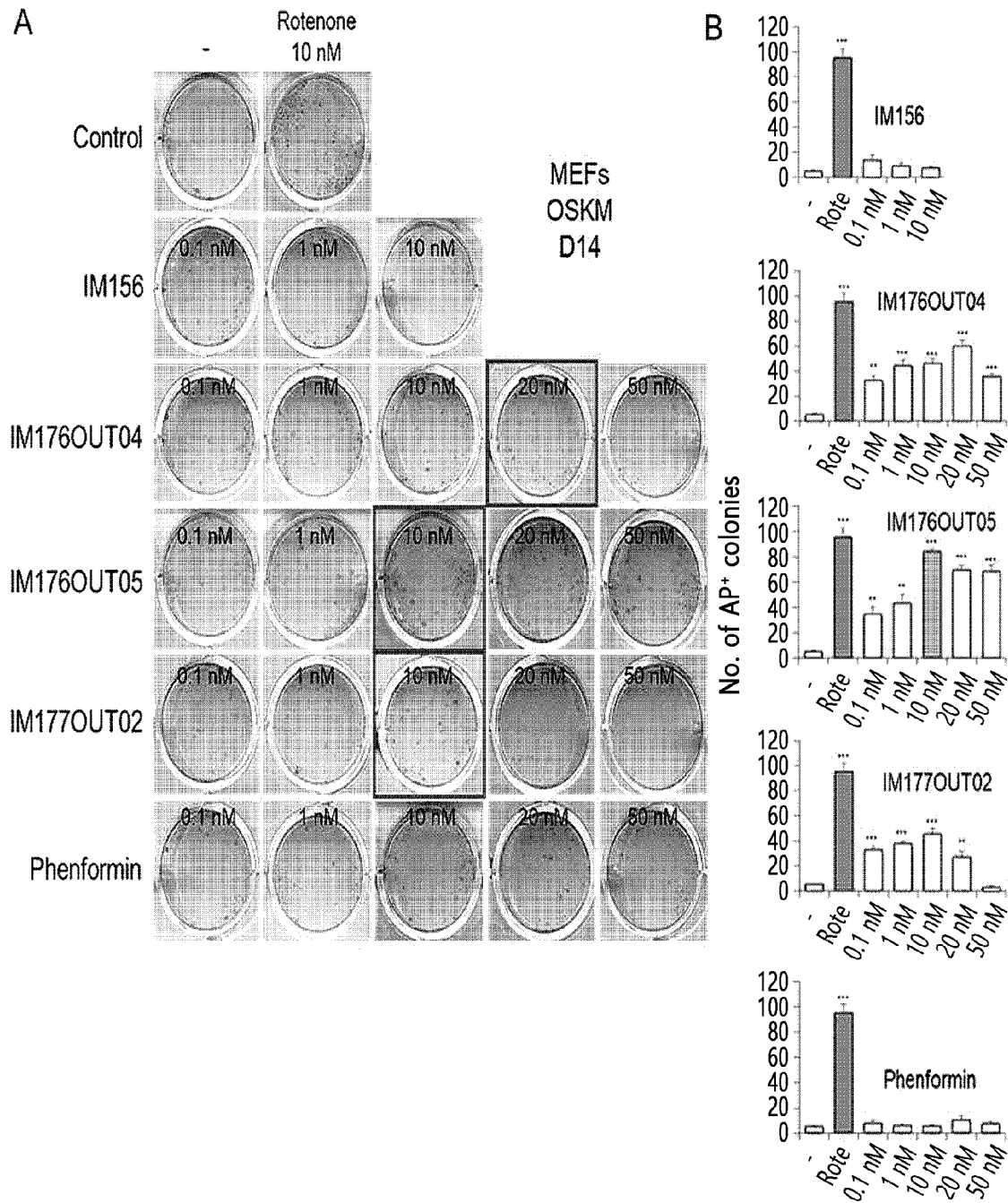

[Fig. 3]
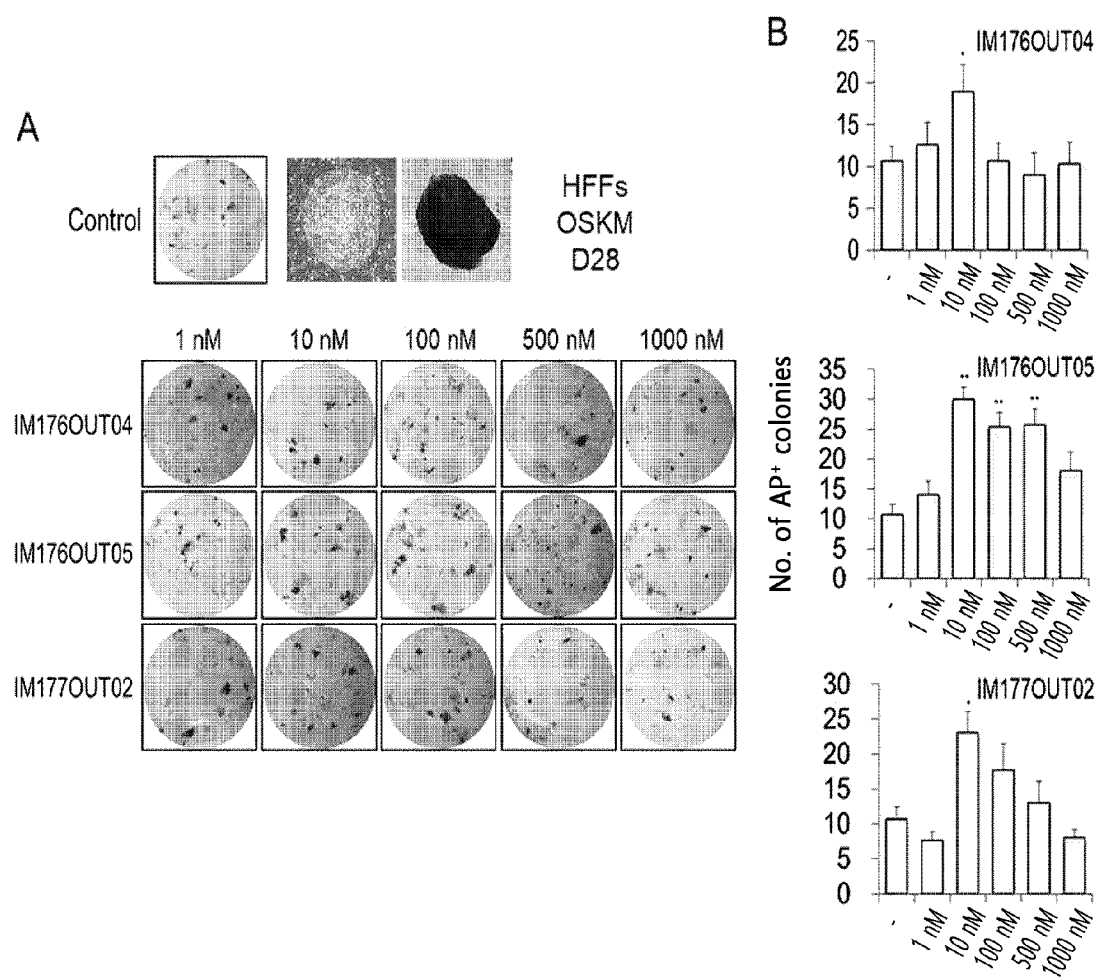

[Fig. 4]
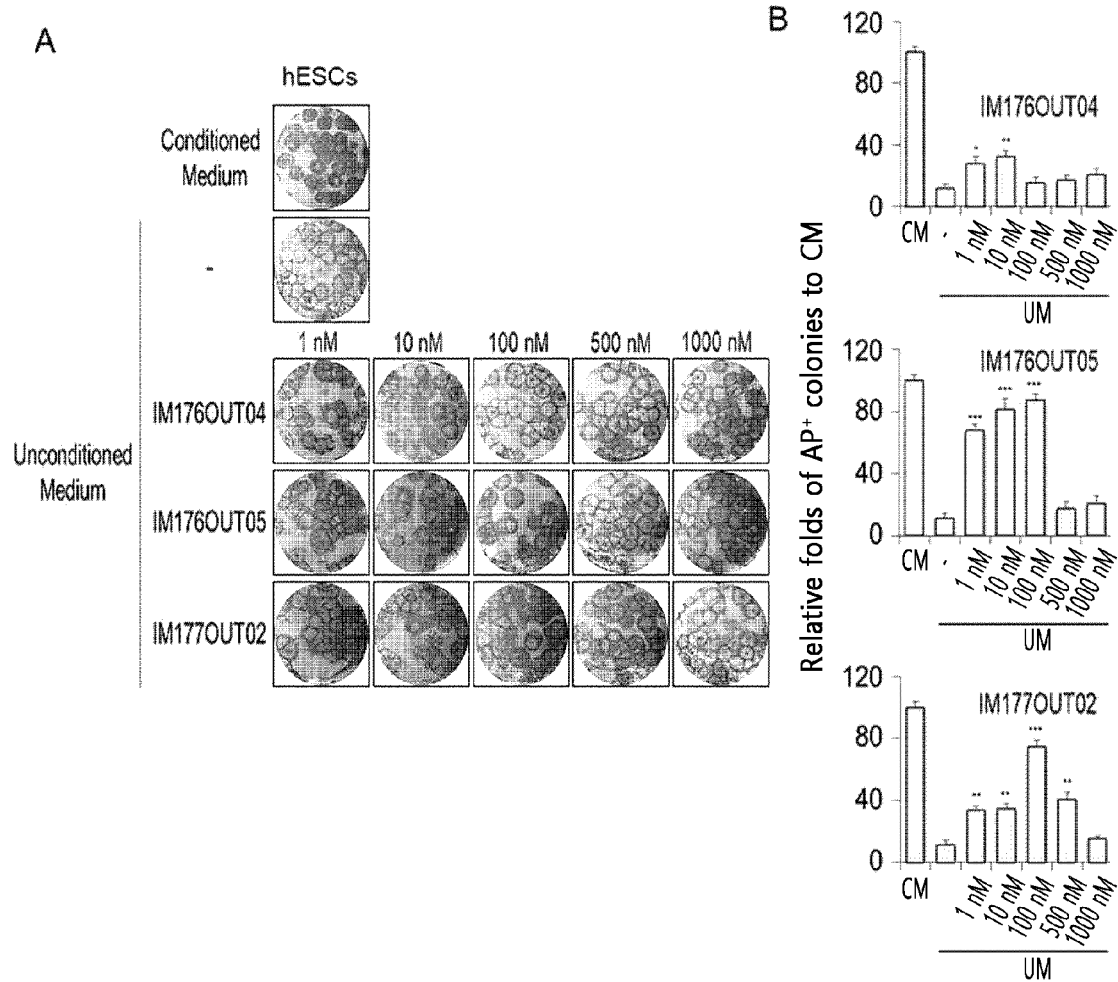

[Fig. 5a]
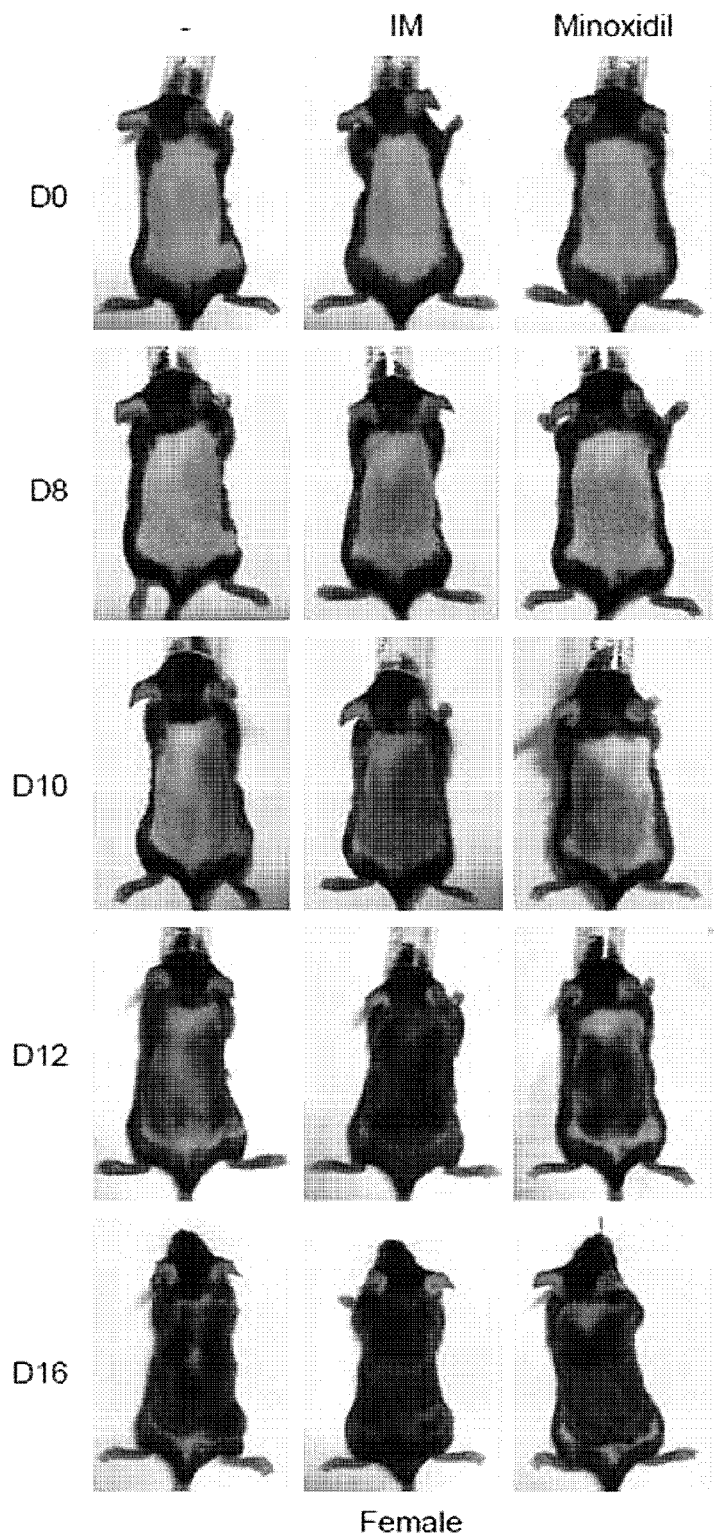

[Fig. 5b]
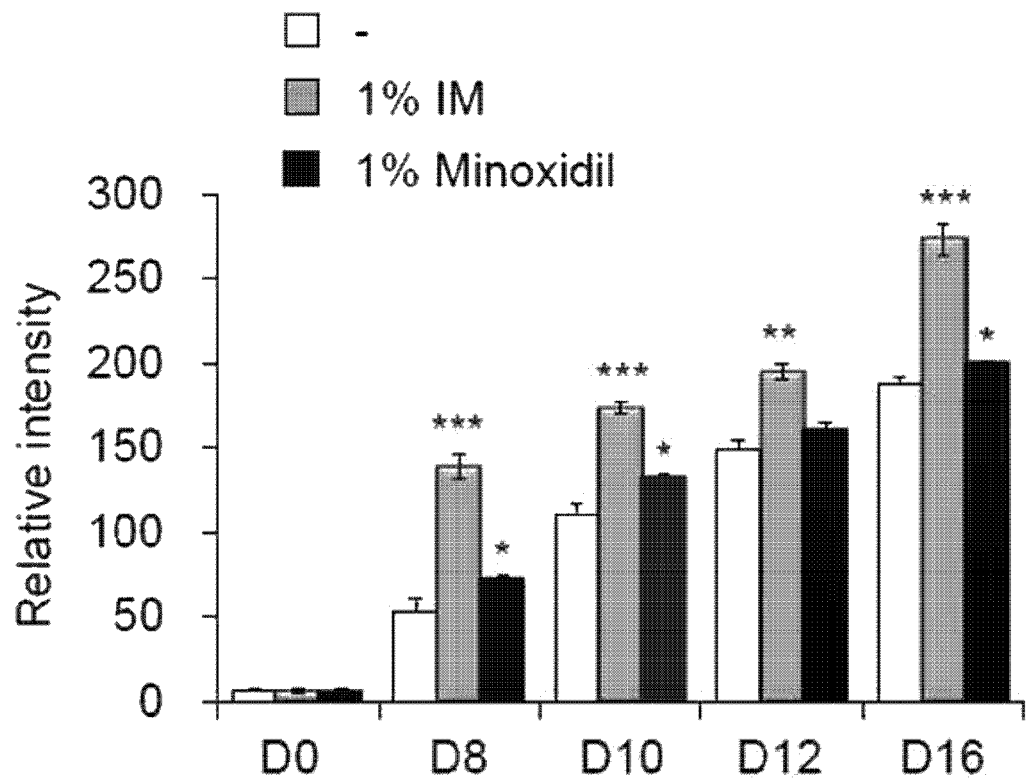
[Fig. 6a]
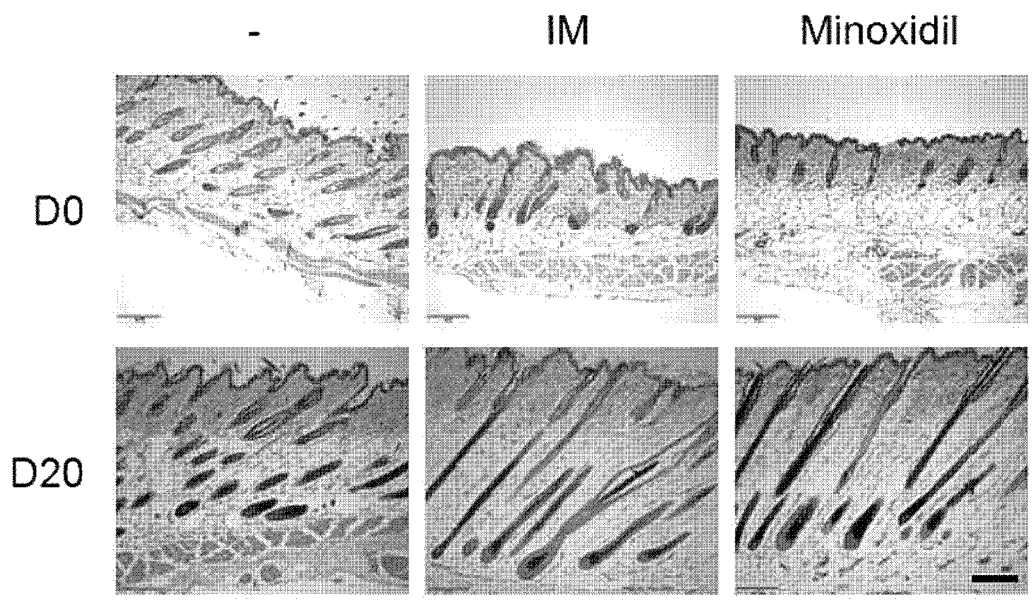

[Fig. 6b]
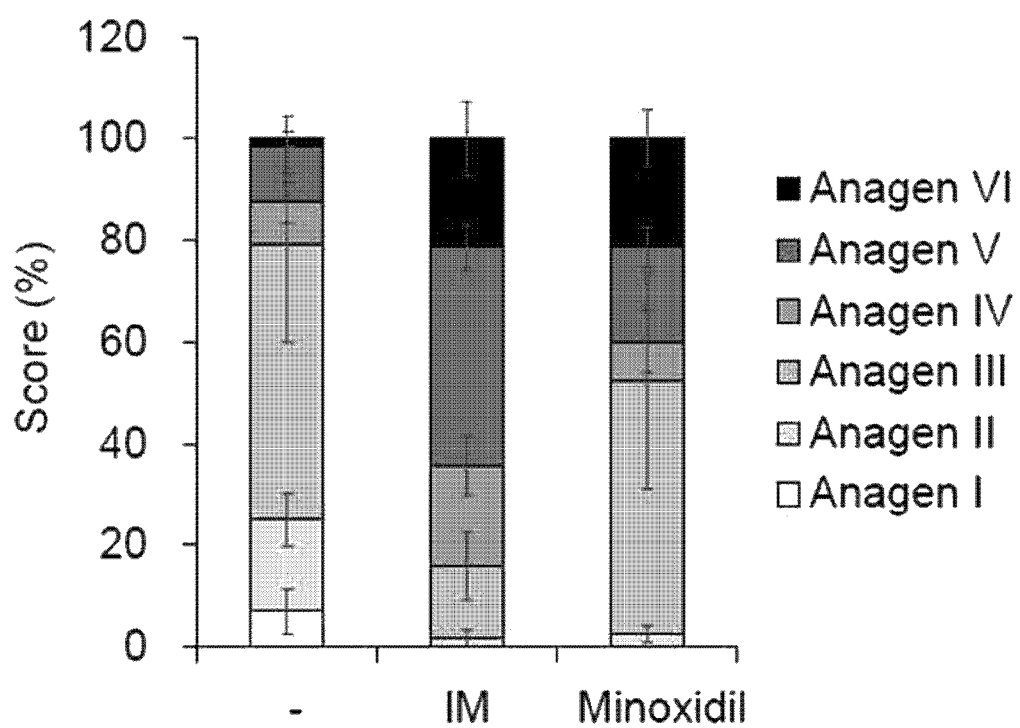

[Fig. 6c]
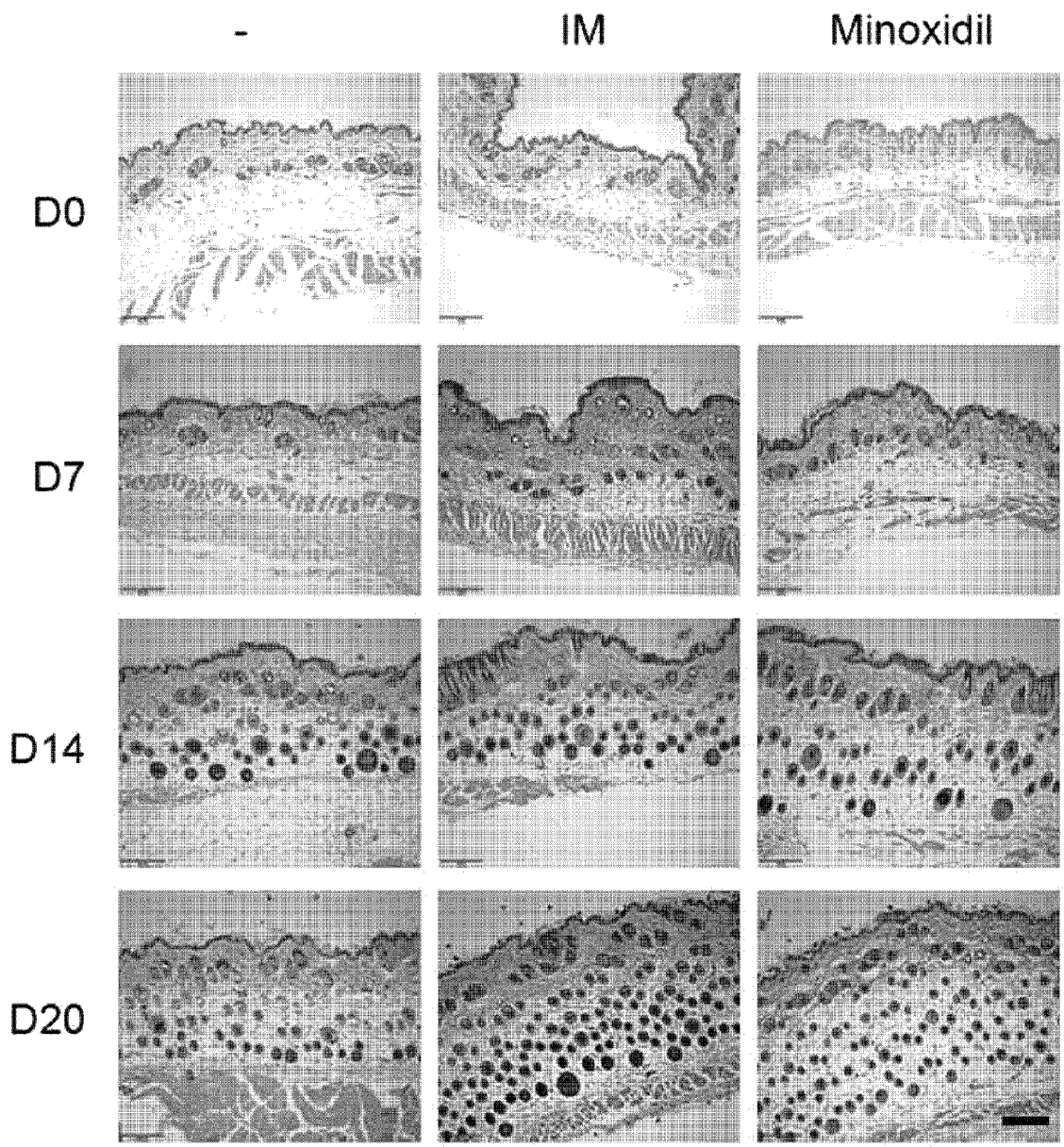

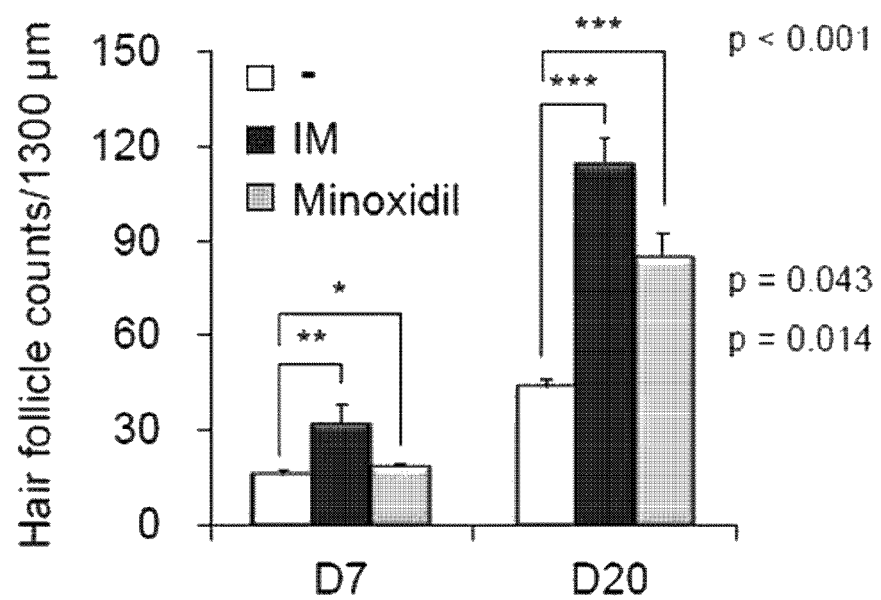

[Fig. 7a]
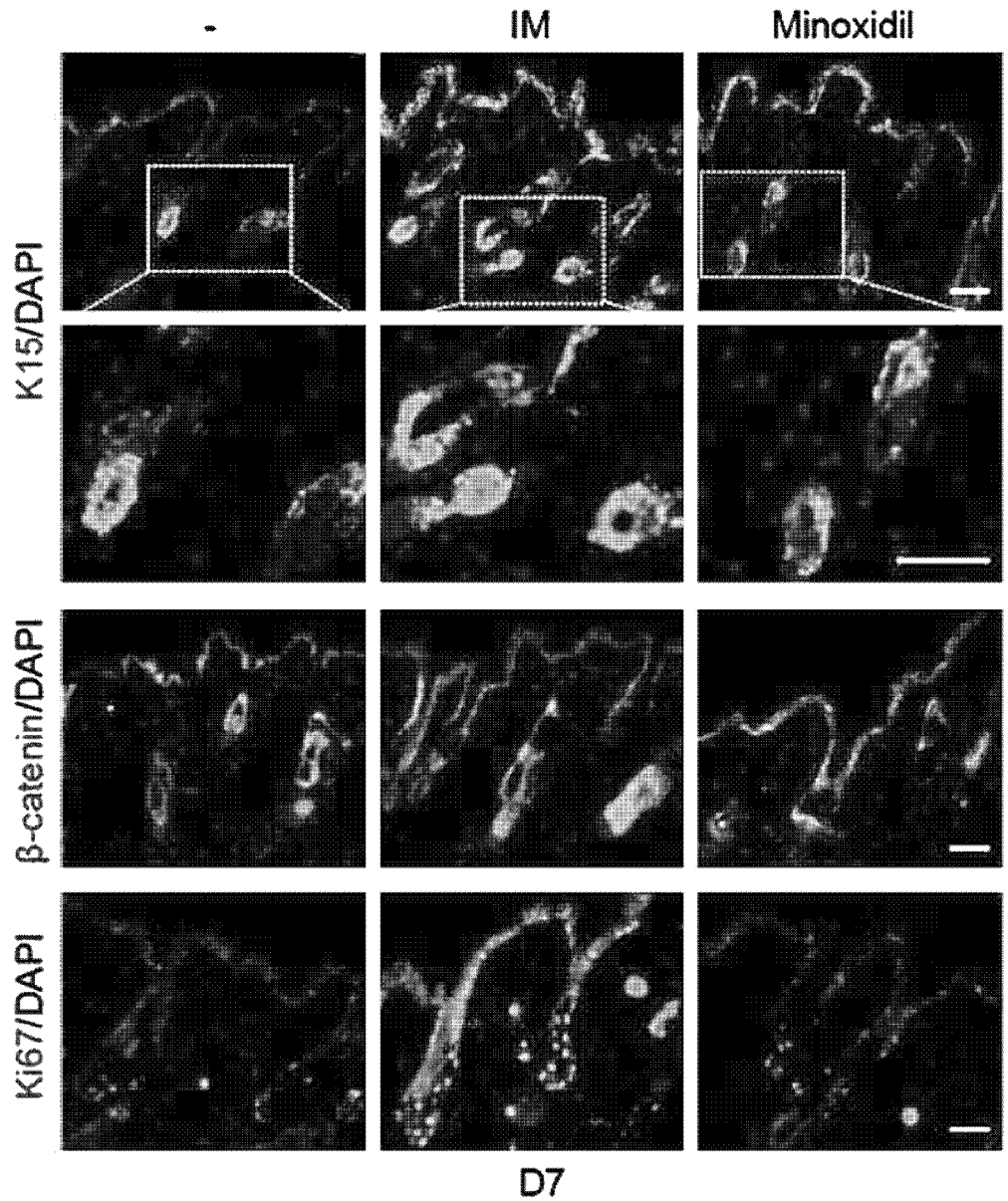

[Fig. 7b]
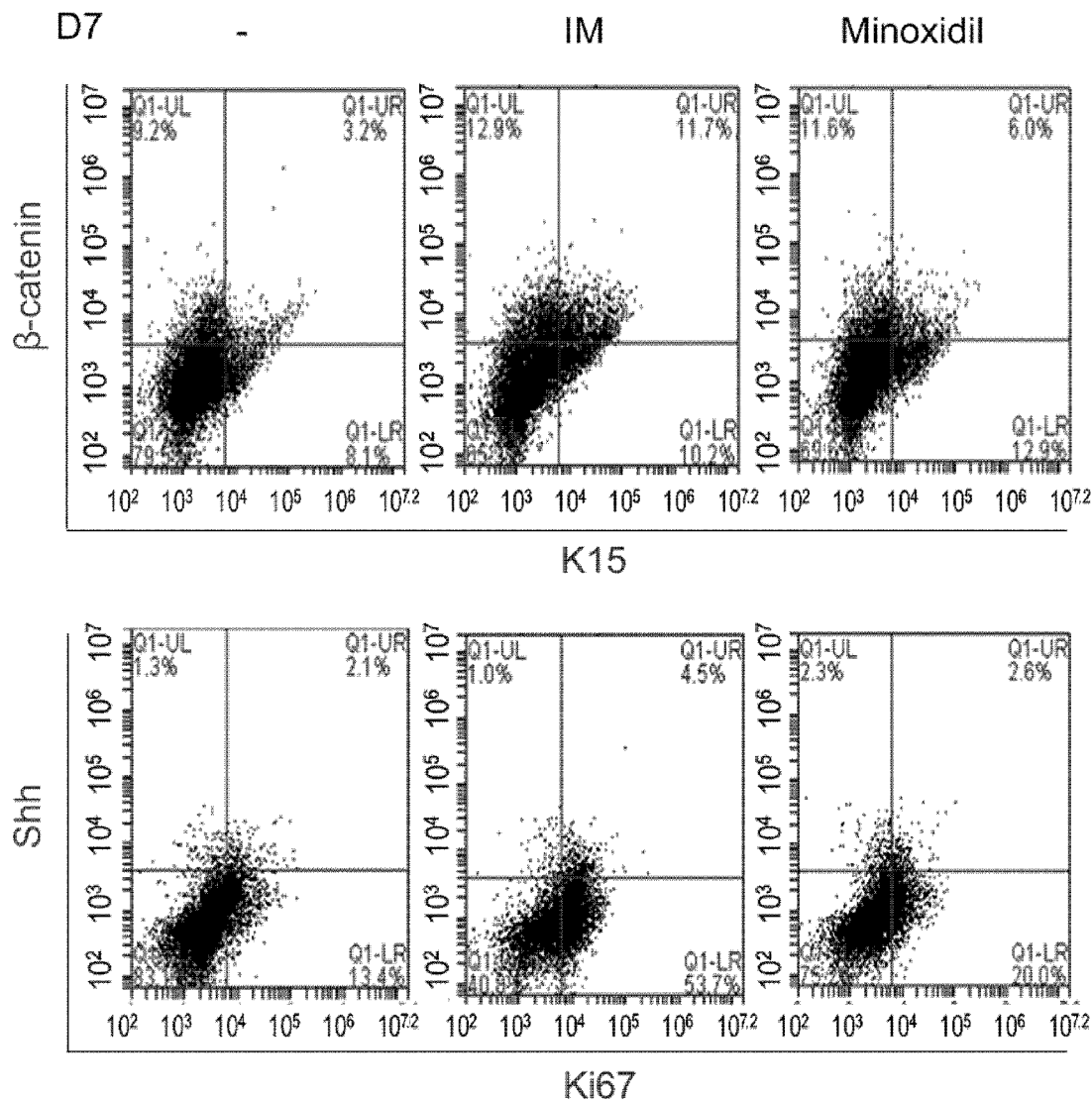

[Fig. 7c]
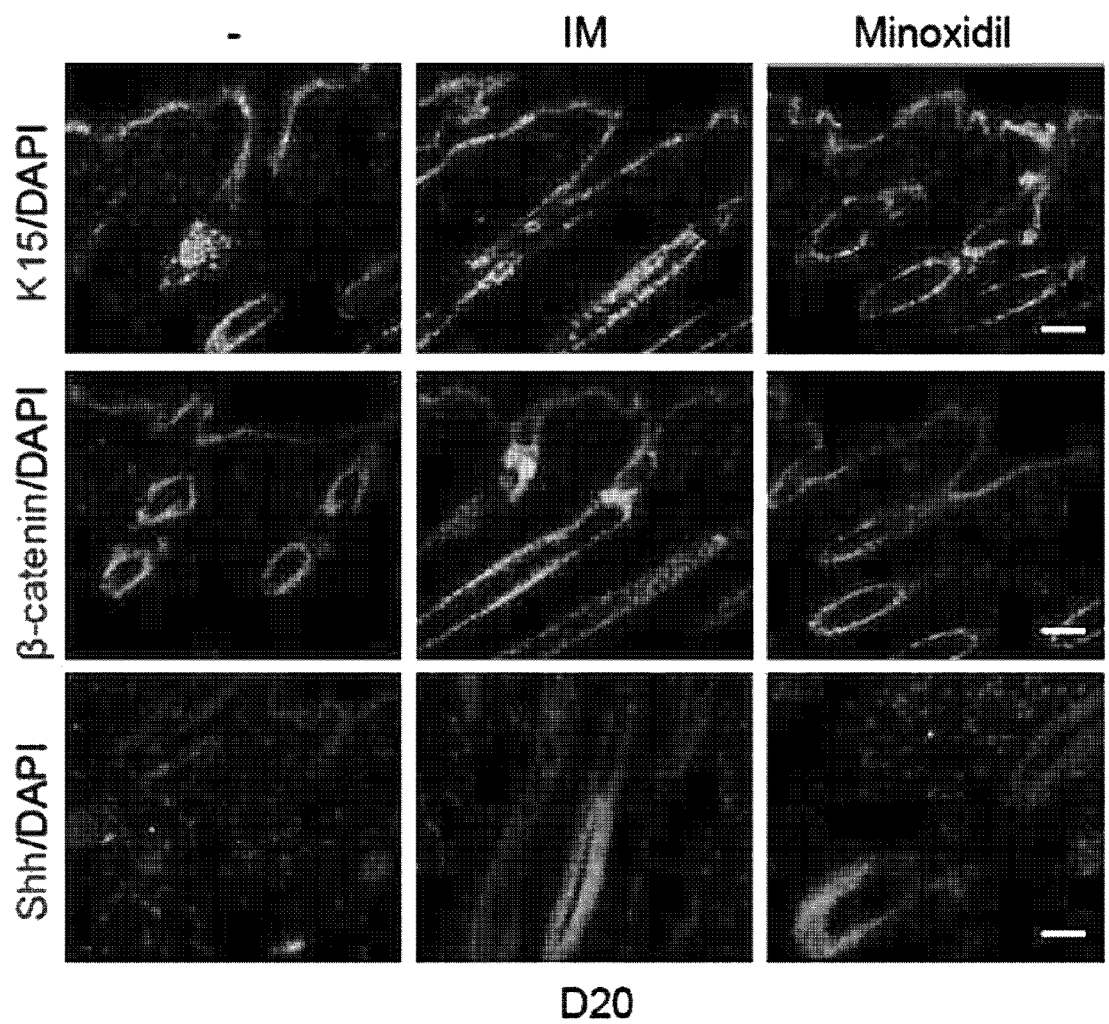

[Fig. 7d]
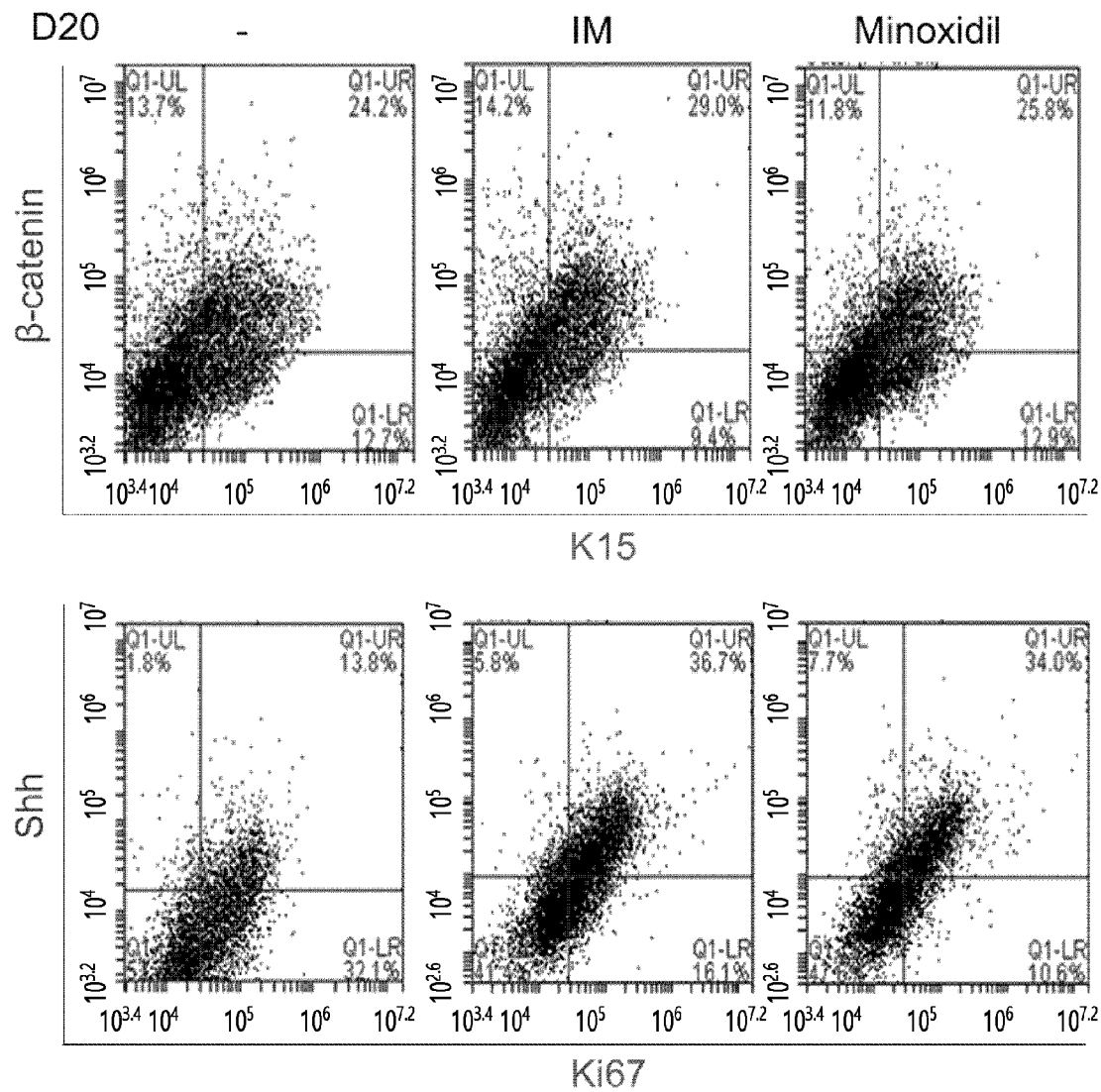

[Fig. 8a]
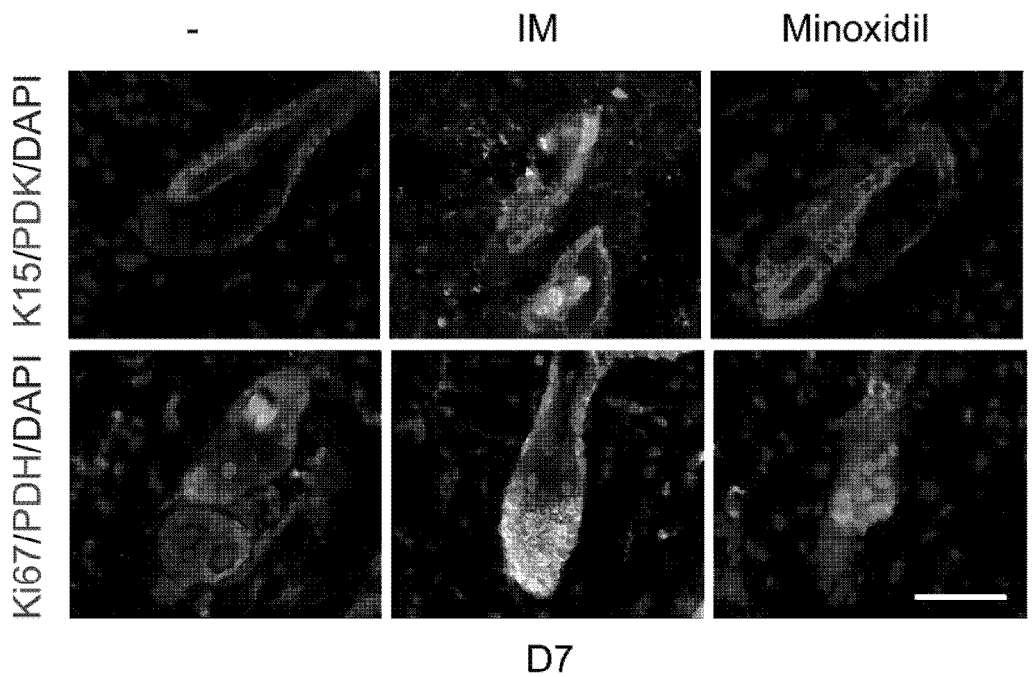
D7
[Fig. 8b]
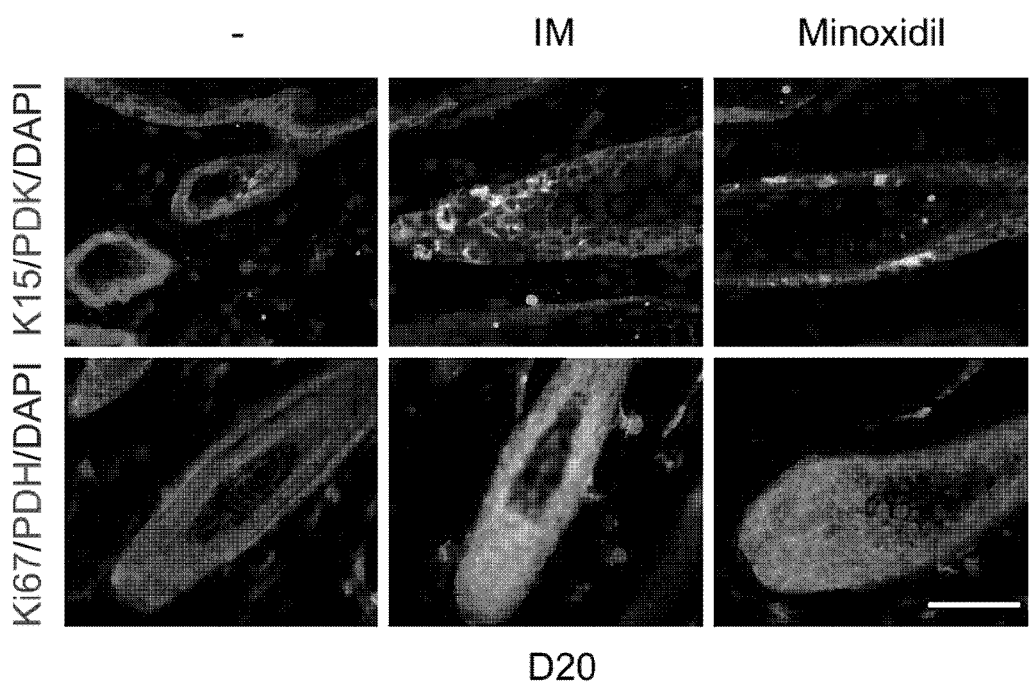
D20

[Fig. 8c]
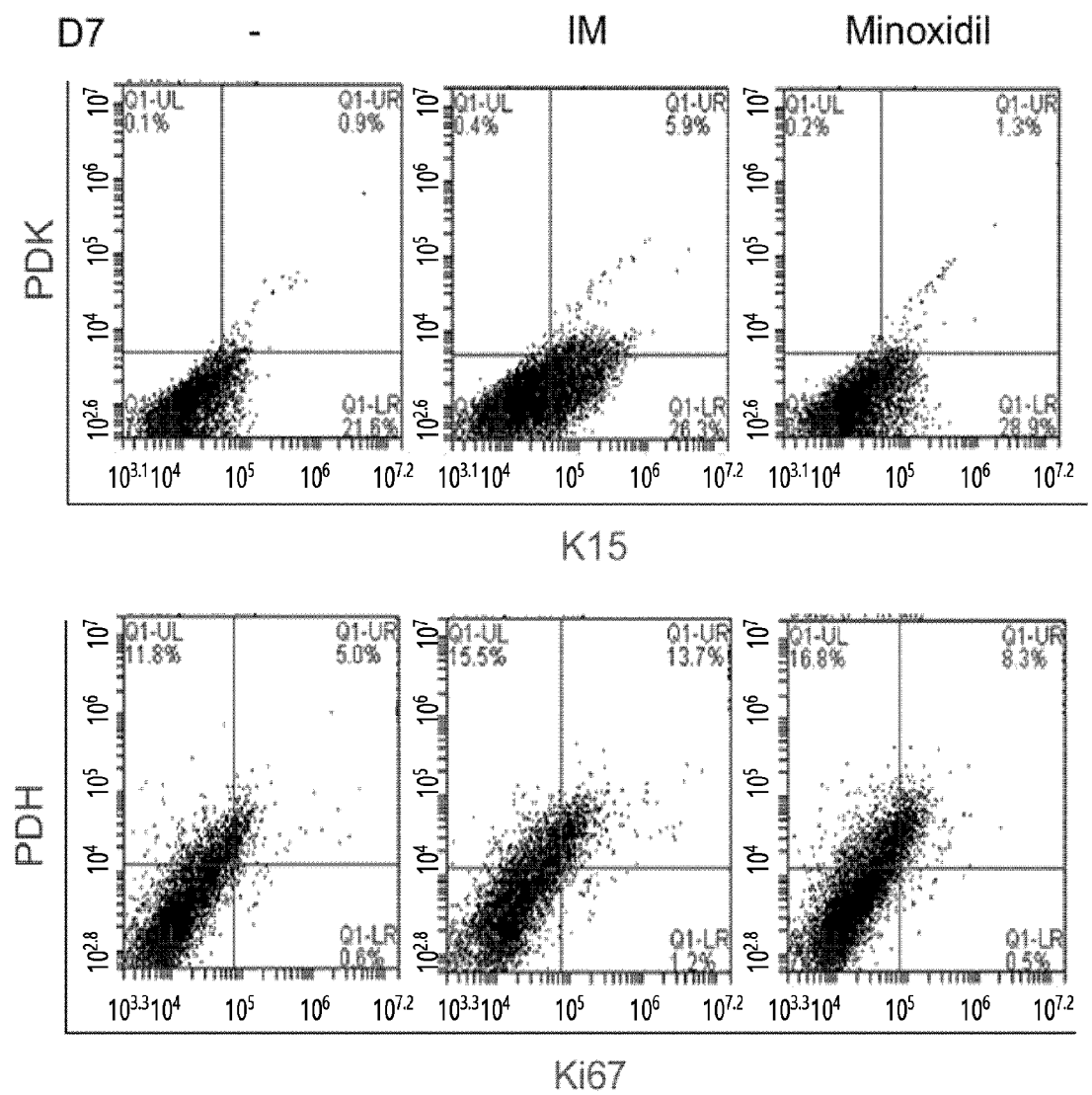

[Fig. 8d]
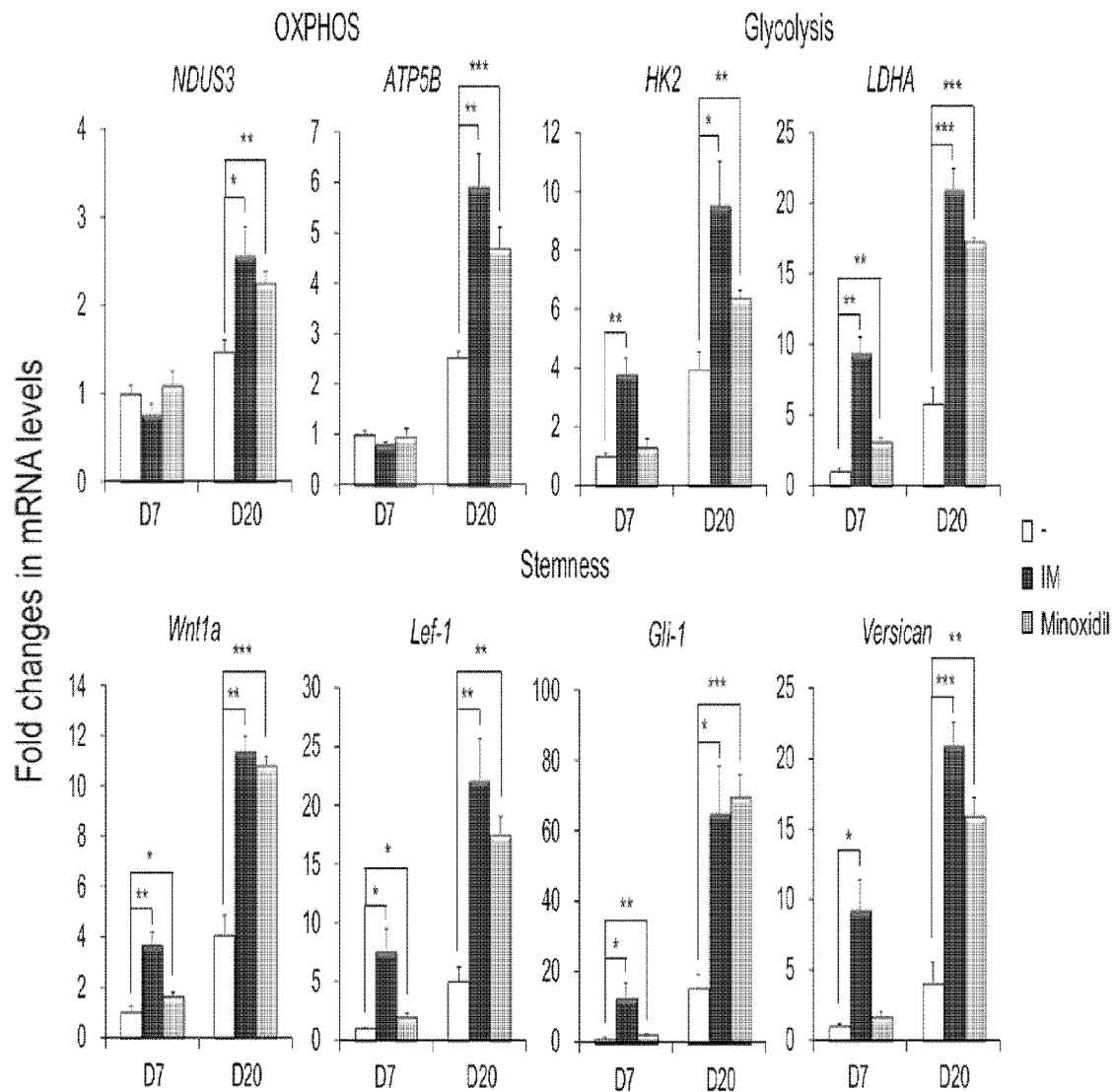

[Fig. 9]
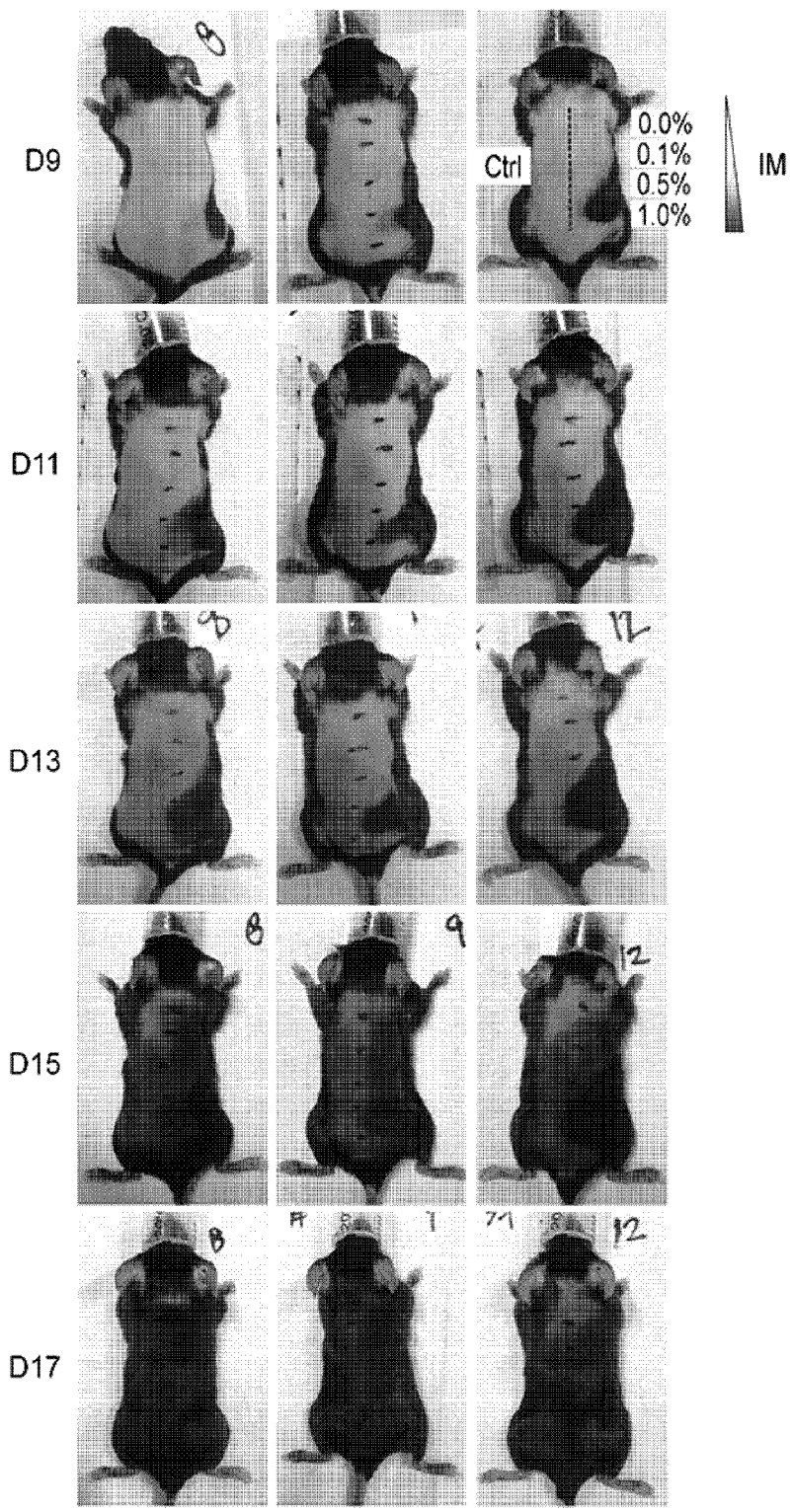

[Fig. 10]
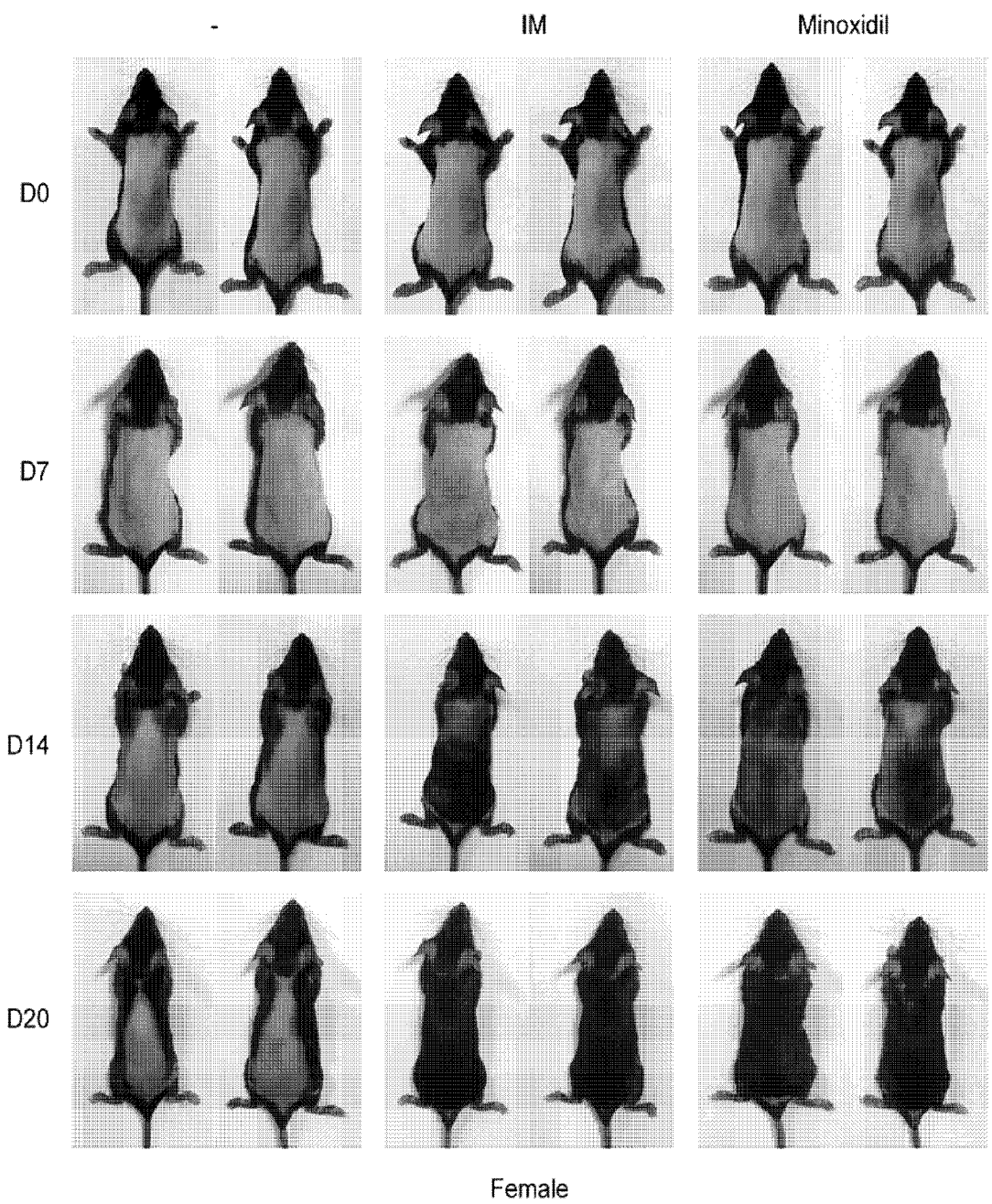
Female

[Fig. 11a]
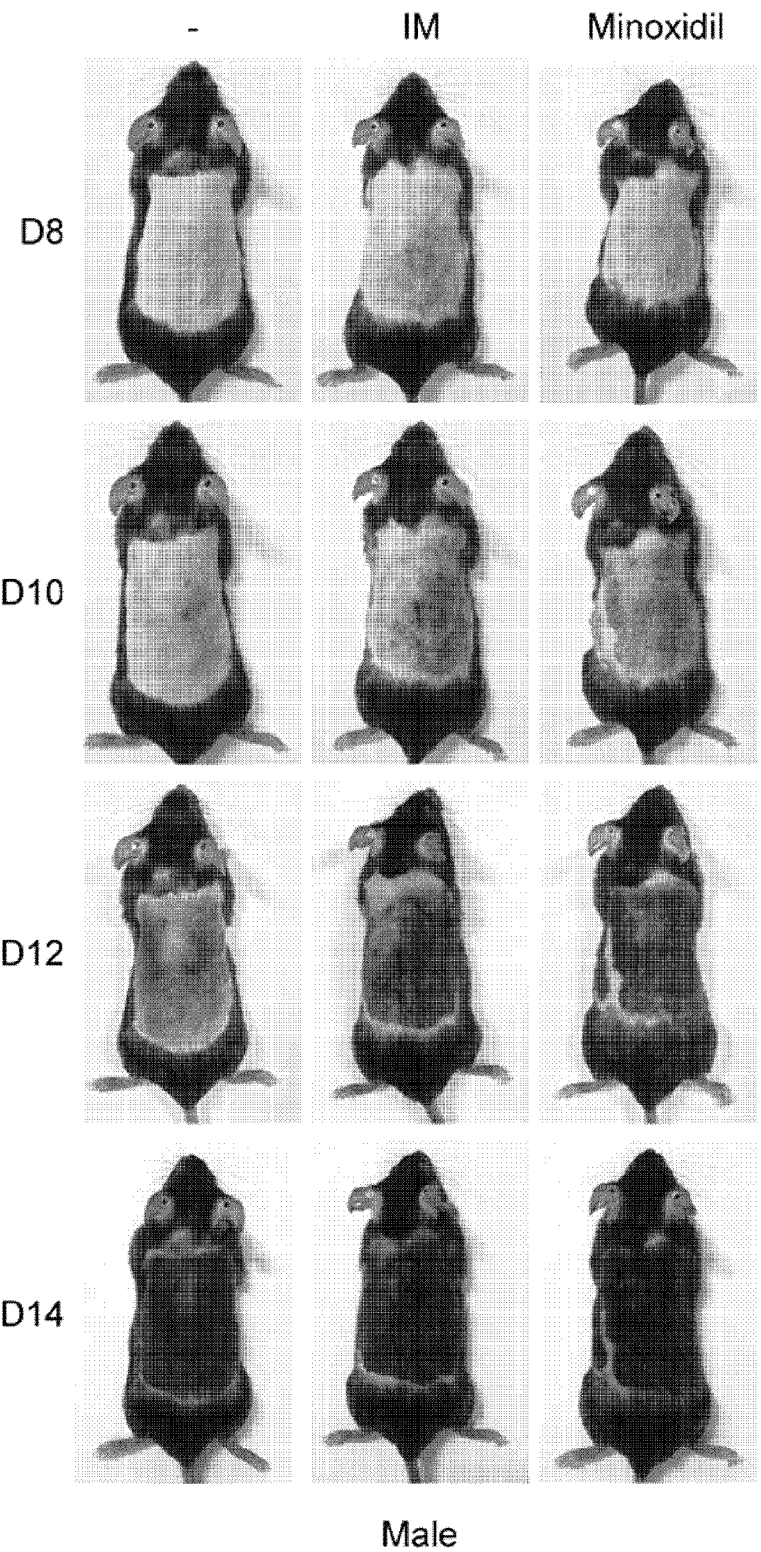

[Fig. 11b]
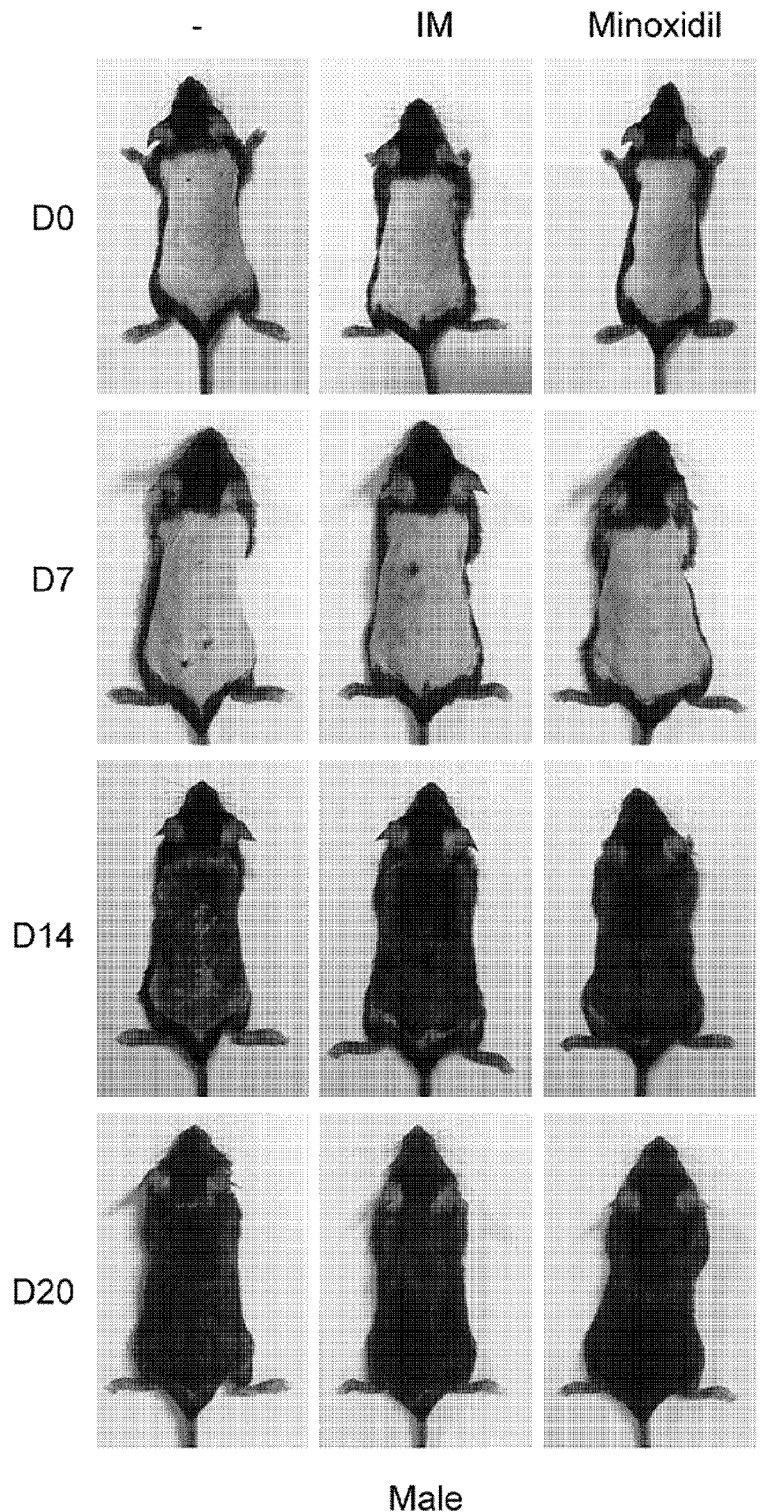
Male

[Fig. 12a]
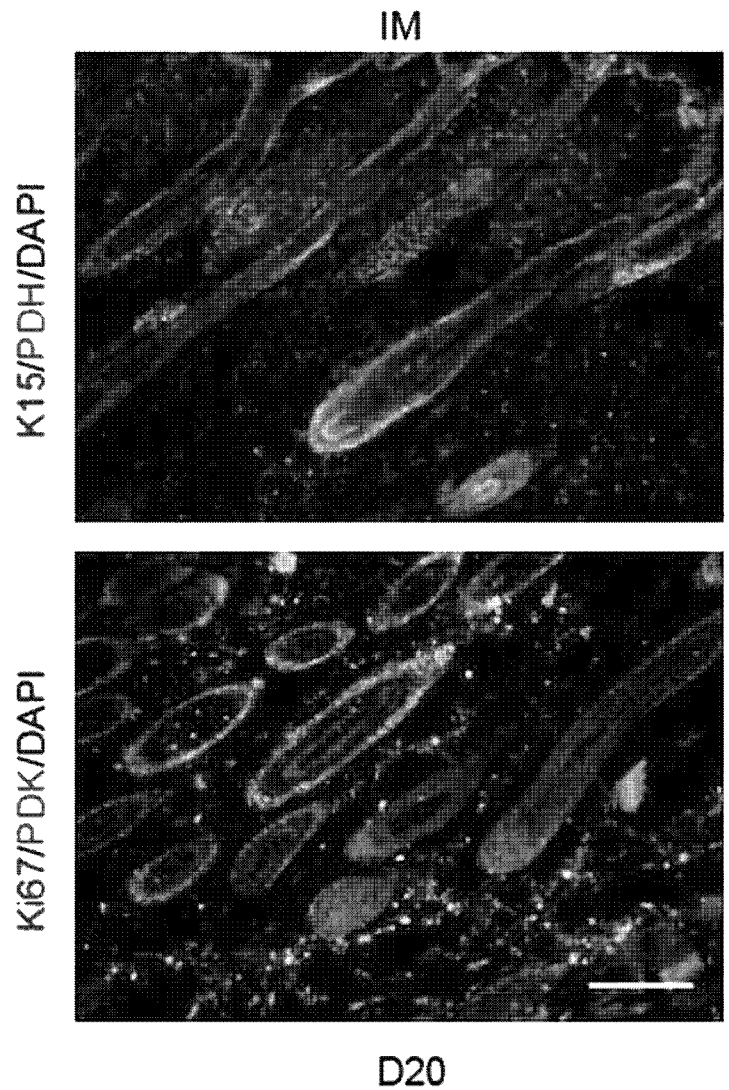

[Fig. 12b]
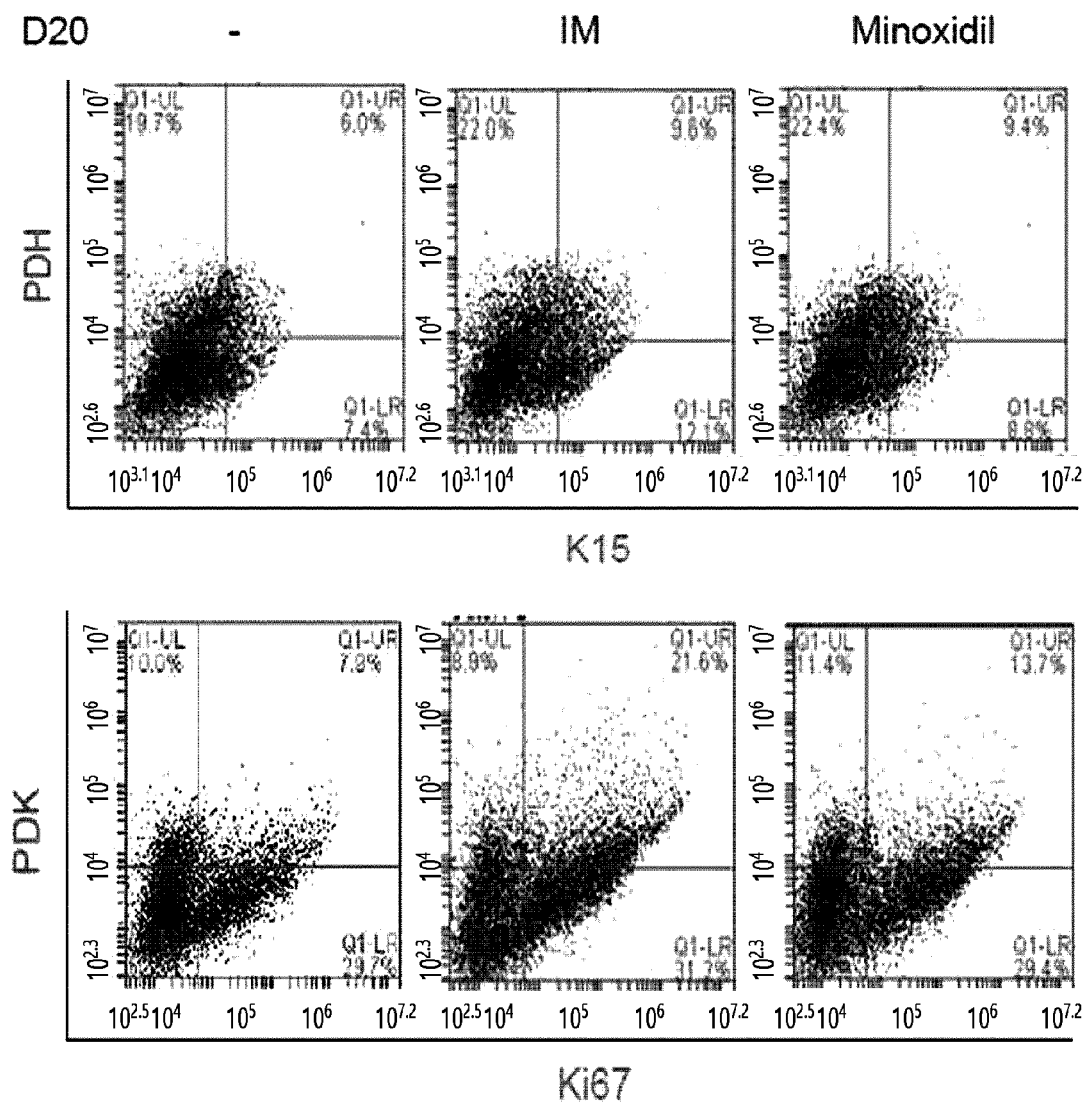

[Fig. 13a]
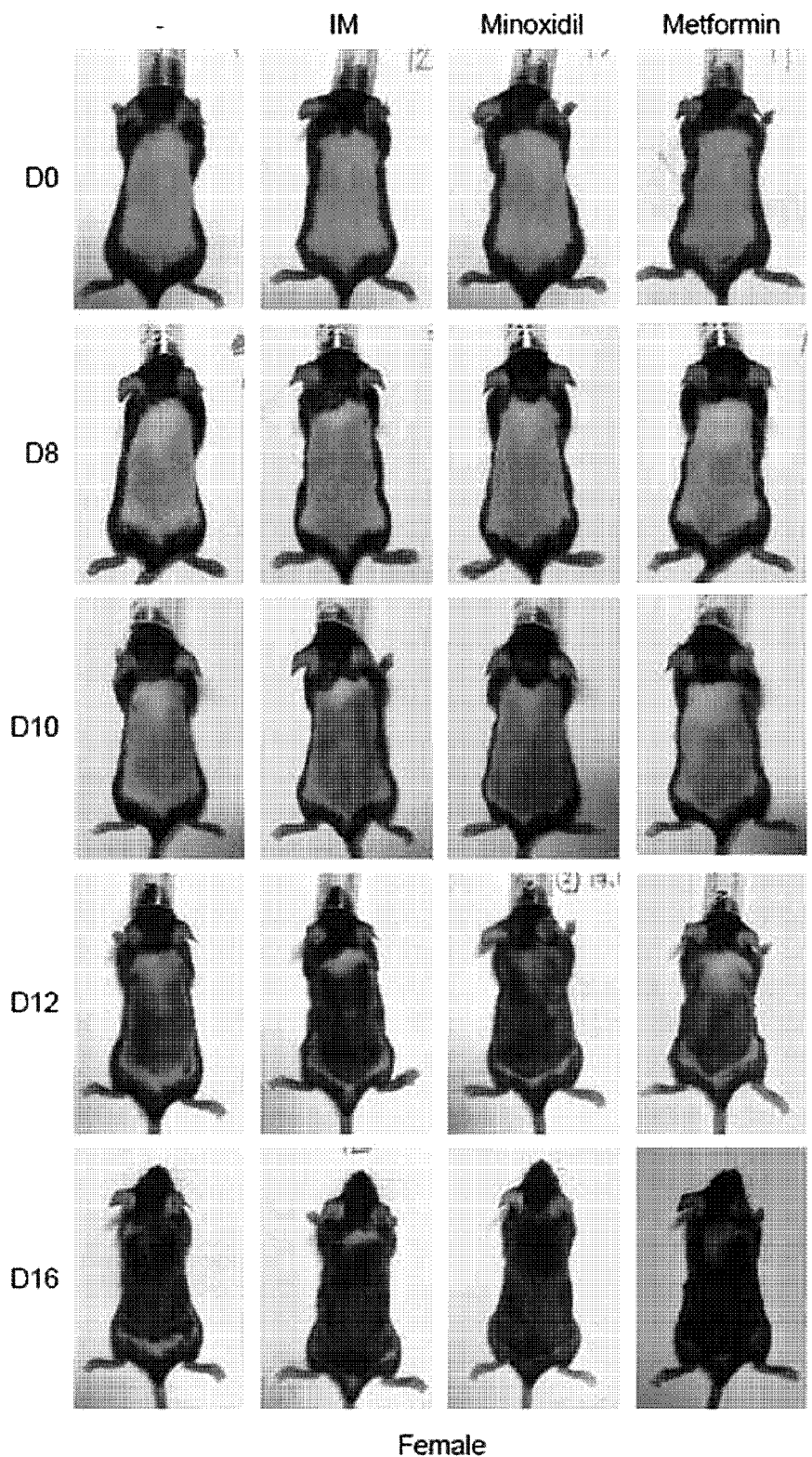

[Fig. 13b]
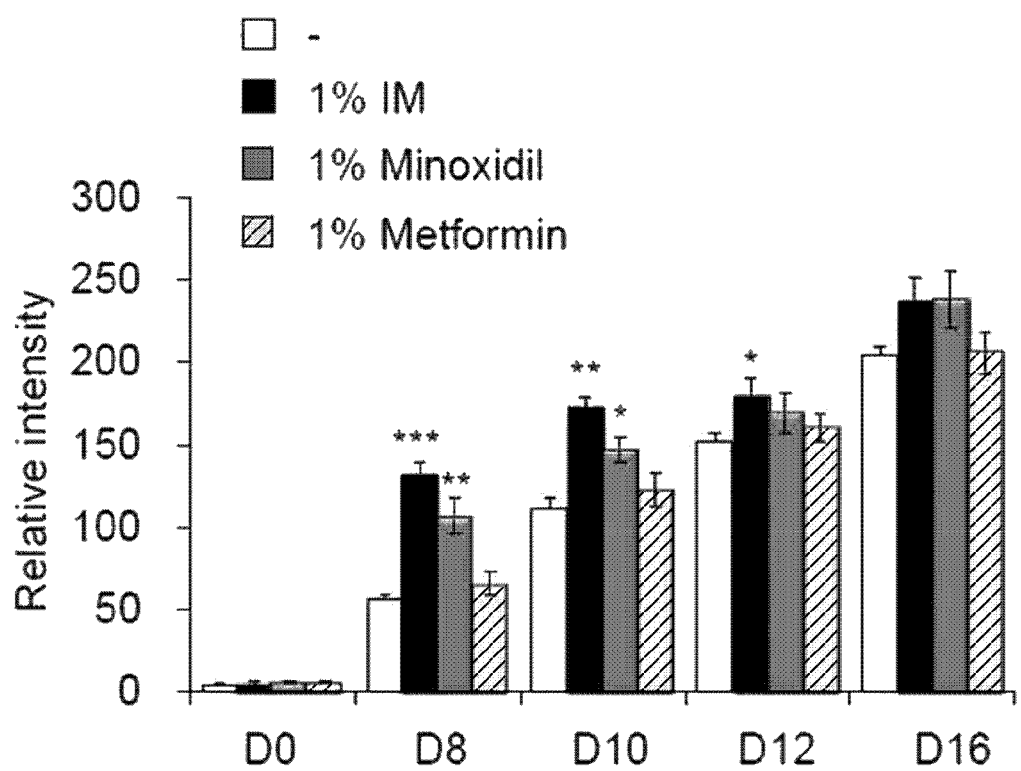

[Fig. 14a]
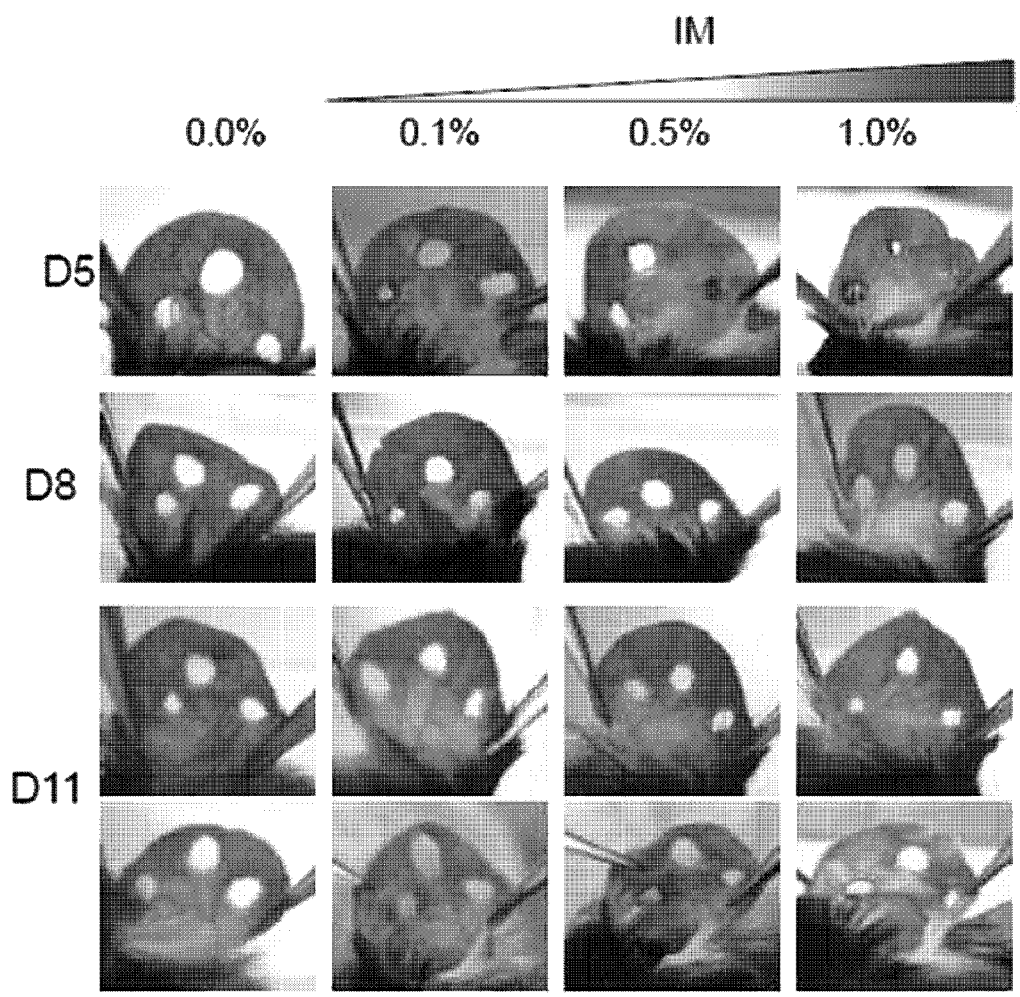

[Fig. 14b]
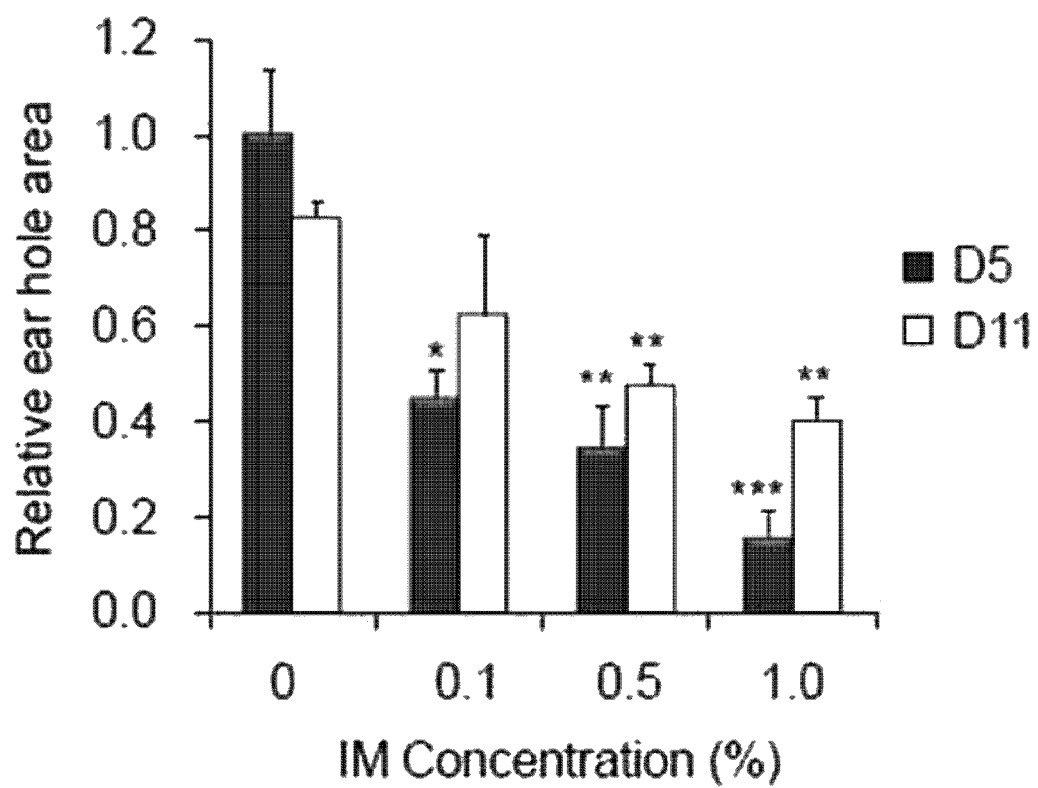

COMPOSITION FOR PROMOTING HAIR GROWTH COMPRISING A GUANINE DERIVATIVE

TECHNICAL FIELD

The present invention relates to a composition for promoting hair growth, and more specifically to a pharmaceutical composition for promoting hair growth comprising a guanine derivative as an active ingredient.

BACKGROUND ART

Hair repeatedly undergoes the three-stage cycle of anagen, which is the growth phase, catagen, which is linked to the regression of the hair, and telogen, which is the resting phase of the hair growth. When the number of hairs in the anagen phase decreases and the ratio of the catagen phase and telogen phase increases, the hair falls out abnormally, leading to hair loss. For the methods for treating hair loss, various attempts including surgical procedures, such as hair transplant surgery, or drug therapy are being made. Although the surgical method provides excellent effects, it has disadvantages in that the cost is high and the surgical procedure may be difficult to perform, which impose significantly large economic and mental burdens on the patient. Additionally, the surgical method is merely a temporary prescription, and thus it cannot be the fundamental method for treating hair loss.

Further, minoxidil, disclosed in U.S. Pat. No. 4,596,812, which is widely used in drug therapy, was originally used as a therapeutic agent for hypertension, but has begun to be used as a hair growth-promoting agent for external use when a side effect of hair growth has been reported. However, minoxidil shows no distinct effect and various side effects such as contact dermatitis, like scalp pruritus, erythema, flaky skin, etc. (Journal of the Korean Medical Association, 56(1), 45). Accordingly, there is a demand for the development of a safe therapeutic agent that has excellent efficacy in preventing hair loss and promoting hair growth while having no side effects.

DISCLOSURE

Technical Problem

The present inventors have established a composition for promoting hair growth, or preventing, treating, and improving hair loss, which can promote hair growth and regenerate hair follicles, using a guanine derivative having no toxicity as an active ingredient, thereby completing the present invention.

Technical Solution

It is one object of the present invention to provide a pharmaceutical composition for promoting hair growth, or preventing or treating hair loss, comprising a guanine derivative or a pharmaceutically acceptable salt thereof as an active ingredient.

It is another object of the present invention to provide a cosmetic composition for promoting hair growth, or preventing or improving hair loss, comprising a guanine derivative or a cosmetically acceptable salt thereof as an active ingredient.

It is still another object of the present invention to provide a food composition for promoting hair growth, or preventing or improving hair loss, comprising a guanine derivative or a sitologically acceptable salt thereof as an active ingredient.

It is even another object of the present invention to provide a feed composition for promoting hair growth, or preventing or improving hair loss, comprising a guanine derivative or a sitologically acceptable salt thereof as an active ingredient.

It is yet another object of the present invention to provide a method for promoting hair growth, or preventing or treating hair loss, comprising administering a pharmaceutical composition comprising a guanine derivative or a pharmaceutically acceptable salt thereof as an active ingredient, to a subject in need thereof.

It is still further another object of the present invention to provide the use of a guanine derivative, a pharmaceutically acceptable salt thereof, or a composition comprising the same as an active ingredient, for promoting hair growth, or preventing or treating hair loss.

It is still further another object of the present invention to provide the use of a guanine derivative, a pharmaceutically acceptable salt thereof, or a composition comprising the same as an active ingredient, for the preparation of medicament for promoting hair growth, or preventing or treating hair loss.

Advantageous Effects

When the composition of the present invention is used, it provides excellent effects of promoting hair growth and regenerating hair follicles compared to commercially available minoxidil. Additionally, the composition of the present invention shows an excellent effect of promoting hair growth compared to conventional guanidine derivatives, and thus can be effectively used in various fields such as pharmaceutical, food, feed, and cosmetic compositions for promoting hair growth, or preventing, treating, and improving hair loss.

DETAILED DESCRIPTION OF EMBODIMENTS

FIG. 1 shows the chemical formulae of guanidine derivatives.

FIG. 2 is a diagram showing the promoting effect of a series of guanidine derivative compounds on reprogramming to iPSCs in mouse embryonic fibroblasts.

FIG. 3 is a diagram showing the promoting effect of a series of guanidine derivative compounds on reprogramming to iPSCs in human foreskin fibroblasts.

FIG. 4 is a diagram showing the promoting effect of a series of guanidine derivative compounds on maintaining stemness of human embryonic stem cells.

FIG. 5a is a diagram confirming the hair growth effect according to the treatment with IM compound in mice with the naked eye.

FIG. 5b is a graph showing the hair growth effect according to the treatment with IM compound in mice.

FIG. 6a shows the results of confirming the effect on the hair follicle cycle according to the treatment with IM compound through H&E staining in the longitudinal section of the mouse skin.

FIG. 6b shows the change in the hair follicle cycle according to the treatment with IM compound.

FIG. 6c shows the results of confirming the effect on the hair follicle cycle according to the treatment with IM compound through H&E staining in the cross section of the mouse skin.

FIG. 6d shows a graph confirming the effect of increasing the number of hair follicles according to the treatment with IM compound.

FIG. 7a is a diagram confirming the expression levels of K15, β-catenin, and Ki67 on the 7$^{th}$ day of treatment with IM compound.

FIG. 7b shows the results of FACS analysis of K15/β-catenin and Ki67/Shh on the 7$^{th}$ day of treatment with IM compound.

FIG. 7c shows the results of histochemical analysis of K15, β-catenin, and Shh on the 20$^{th}$ day of treatment with IM compound.

FIG. 7d shows the results of FACS analysis of K15/β-catenin and Ki67/Shh on the 20$^{th}$ day of treatment with IM compound.

FIG. 8a shows the results of comparing the histochemical analysis of K15, PDK, Ki67, and PDH on the 7$^{th}$ day of treatment with IM compound and minoxidil.

FIG. 8b shows the results of comparing the histochemical analysis of K15, PDK, Ki67, and PDH on the 20$^{th}$ day of treatment with IM compound and minoxidil.

FIG. 8c shows the results of comparing the FACS analysis of K15/PDK and Ki67/PDH on the 7$^{th}$ day of treatment with IM compound and minoxidil.

FIG. 8d shows the result of comparing the expression level of OXPHOS-related enzymes (NDUS3 and ATP5B), glycolysis-related enzymes (HK2 and LDHA) and stemness-related genes (Wnt1a, Lef-1, Gli-1, and versican) upon treatment with IM compound and minoxidil.

FIG. 9 is a diagram confirming the hair growth effect according to the treatment with IM compound in mice with the naked eye.

FIG. 10 is a diagram confirming the hair growth effect according to the treatment with IM compound in female mice with the naked eye.

FIG. 11a is a diagram confirming the hair growth effect according to the treatment with IM compound in male mice with the naked eye.

FIG. 11b is a diagram confirming the hair growth effect according to the treatment with IM compound in male mice.

FIG. 12a shows the results of histochemical analysis of K15, PDK, Ki67, and PDH on the 20$^{th}$ day of treatment with IM compound.

FIG. 12b shows the results of comparing the FACS analysis of K15/PDH and Ki67/PDK on the 20$^{th}$ day of treatment with IM compound and minoxidil.

FIG. 13a is a diagram comparing the hair growth effect according to the treatment with IM compound and metformin in mice with the naked eye.

FIG. 13b is a graph comparing the hair growth effect according to treatment with IM compound and metformin in mice.

FIG. 14a is a diagram confirming the tissue repair effect of the auricle according to the treatment with IM compound.

FIG. 14b is a graph showing the tissue repair effect of the auricle according to the treatment with IM compound.

DETAILED DESCRIPTION OF EMBODIMENTS

One aspect of the present invention provides a pharmaceutical composition for promoting hair growth, or preventing or treating hair loss, comprising a compound of Chemical Formula 1 below, or a pharmaceutically acceptable salt thereof as an active ingredient:

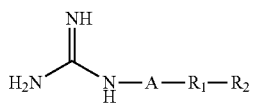

[Chemical Formula 1]

wherein in Chemical Formula 1 above,

A is a single bond or —C(NH)—NH—, $R_1$ is —$(CH_2)_n$—, wherein n is an integer of 1 to 4, $R_2$ is $C_6$-$C_{10}$ aryl which is unsubstituted or substituted with one or more substituent(s) selected from halogen or $C_1$-$C_4$ alkyl.

For example, the compound may be any one of compounds of Chemical Formulae 2 to 4 below:

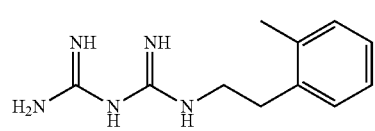

[Chemical Formula 2]

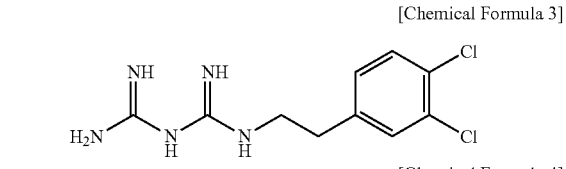

[Chemical Formula 3]

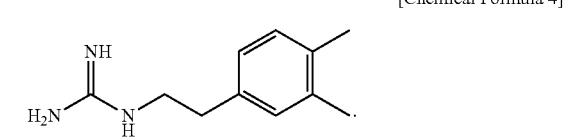

[Chemical Formula 4]

The compounds of Chemical Formulae 2 to 4 are hydrophobic cationic small molecules having a guanidine or a biguanide core, and their chemical names are (N-1-(2-methyl)phenethylbiguanide, N-1-(3,4-dichloro)phenethylbiguanide, and 1-(3,4-dimethylphenethyl)guanide, respectively. In the following examples, these compounds are referred to as "IM176OUT05" (or "IM"), "IM176OUT04", and "IM177OUT02", respectively.

The compound of Chemical Formula 1 or a pharmaceutically acceptable salt thereof according to the present invention can promote reprogramming of somatic cells in animals including humans and maintain stemness, and further accelerates hair follicle regeneration and increases the number of hair follicles by promoting the progression of the hair follicle cycle, and thus has the effects of promoting hair growth and preventing or treating hair loss.

For example, it is known that the stemness of cells plays an important role in the formation of hair and/or hair follicles especially through the R-catenin signaling process, and thus, imparting and maintaining the stemness property is a factor responsible for regulating hair growth, hair regeneration, and/or formation of hair follicles (Nature Cell Biology, 2017, 19:1017-1027; In vivo, 2019, 33:1209-1220). In this regard, in a specific example of the present invention, it was confirmed that the guanidine derivative compounds can promote reprogramming of somatic cells and maintain stemness of stem cells, which implies that these compounds exert the effects of promoting hair growth and preventing or treating hair loss by regulating hair growth, hair regeneration, and/or formation of hair follicles.

Further, in order to confirm these findings more specifically, these compounds were applied at the cellular level and further to animal models, and as a result, it was confirmed that the compounds increased the β-catenin expression in the hair follicles and the number of hair follicles, and showed the effect of promoting actual hair regeneration and/or hair growth.

As used herein, the term "promoting hair growth" refers to the production of hair, and is used to increase the rate of hair production and the amount of hair production. In addition, the term means that the functions of hair root are enhanced, or the number of hairs growing in hair follicles is increased due to the shortening of the hair falling and production cycle, and further, it means that the number of hair follicles is increased.

The pharmaceutical composition may have an excellent efficacy in promoting hair growth by shortening the telogen phase in the hair growing and falling cycle and promoting the entry into the anagen phase, as compared to minoxidil, which is used as a conventional hair growth promoter. In addition, the composition did not show any side effects including skin problems.

In one embodiment of the present invention, the pharmaceutical composition may comprise the compound of Chemical Formula 1 or a pharmaceutically acceptable salt thereof in a concentration of 1% to 5%, specifically in a concentration of 1% to 4% or 1% to 3%.

In one embodiment of the present invention, the pharmaceutical composition may promote reprogramming of a cell or maintain stemness of a cell. Additionally, the pharmaceutical composition may promote the regeneration of hair follicles and hair growth. In one embodiment of the present invention, the composition may enhance the expression of any one or more selected from the group consisting of R-catenin, Shh (sonic hedgehog), HK2 (hexokinase 2), LDHA (lactate dehydrogenase A), NDUS3 (NADH dehydrogenase iron-sulfur protein 3), ATP5B (ATP synthase subunit beta), Wnt1a, Lef-1 (lymphoid enhancer binding factor 1), Gli-1 (GLI family zinc finger 1), versican, PDH (pyruvate dehydrogenase), and PDK (pyruvate dehydrogenase kinase).

Specifically, the pharmaceutical composition may increase the expression level of B-catenin and Shh, which mediate the regeneration and development of hair follicles, glycolysis-related enzymes HK2 and LDHA, OXPHOS-related enzymes NDUS3 and ATP5B, and stemness-related genes Wnt1a, Lef-1, Gli-1, and versican, which are involved in the hair follicle development, and may also increase the expression of PDK, an enzyme that promotes the conversion of glycolysis, and PDH, an enzyme that responds to mitochondrial OXPHOS. This implies that the composition can have an excellent effect in promoting hair growth by promoting the expression of these factors with significantly increased effect compared to minoxidil, which is used as a conventional hair growth promoter.

The pharmaceutical composition can promote the expression of genes related to hair follicle development and activate various signals for hair regeneration. In addition, the composition can promote glycolysis by directly stimulating the metabolism of stem cells, thereby further promoting OXPHOS. Based on the findings, the pharmaceutical composition can contribute to the metabolism of active energy required for hair growth.

The pharmaceutical composition of the present invention may be administered in a pharmaceutically effective amount. As used herein, the term "pharmaceutically effective amount" refers to an amount sufficient to treat a disease at a reasonable benefit/risk ratio applicable to any medical treatment, and it may be determined based on the factors including the type and severity of a disease, age, gender, the activity of a drug, the sensitivity to a drug, an administration time, an administration route and an excretion rate, a duration of treatment, drugs used simultaneously, and other factors well known in the medical field.

The pharmaceutical composition may be administered as an individual therapeutic agent or in combination with other therapeutic agents, and may be administered sequentially or simultaneously with a conventional therapeutic agent. In view of all of the above elements, it is important to administer the composition at a dose in which the maximum effect can be achieved with the minimum amount without adverse effects, and the dose of the composition may be easily determined by those skilled in the art. For example, the dose may be increased or decreased depending on a route of administration, the severity of a disease, the gender, body weight, age of a patient, etc., and thus, the dose is not intended to limit the scope of the present invention in any way.

As used herein, the term "pharmaceutically acceptable salt" refers to any salt possessing a desired biological and/or physiological activity of the compound, and exhibiting a minimum of unwanted toxicological effects. The salt may be an acid addition salt formed by an organic acid or inorganic acid. The organic acid may include, for example, formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranilic acid, dichloroacetic acid, aminooxy acetic acid, benzensulfonic acid, p-toluenesulfonic acid, and methanesulfonic acid. Additionally, the inorganic acid may include, for example, hydrochloric acid, bromic acid, sulfuric acid, phosphoric acid, nitric acid, carbonic acid, and boric acid, and may be preferably in the form of hydrochloride or acetate, and more preferably in the form of hydrochloride.

For example, the composition according to the present invention may further include proper carriers, excipients, and diluents commonly used for the preparation of pharmaceutical compositions. The composition may be sterilized or aseptic, and the solution may be sterilized or aseptic, may be water, a buffer, an isotonic agent, etc., or may include other ingredients known to those skilled in the art, which do not cause allergies or other harmful reactions when applied to animals or humans.

As used herein, the term "pharmaceutically acceptable carrier" includes all random solvents, dispersive media, coating materials, antimicrobial agents, antifungal agents, isotonic agents, etc. Using the media and the formulations as pharmaceutically active materials is well known in the related art. In addition to common media or formulations which are non-miscible with active ingredients, the use of the media and the formulations described above is considered in therapeutic compositions. Additionally, supplementary active ingredients may be mixed with the composition described above.

The composition may be prepared as formulations such as liquids, emulsions, suspensions, or creams, or may be used for non-oral administration. The amount of the composition used may be an amount commonly used for preventing or treating hair loss, and is preferably different depending on the age, gender, and condition of a patient, in vivo absorbance of active substances, inactivation rate, drugs used in combination, etc.

In one embodiment of the present invention, the pharmaceutical composition is preferably formulated as a preparation for parenteral administration, and may be formulated as an external skin preparation or subcutaneous injection which is used topically on a region where hair growth is desired.

In one embodiment of the present invention, the external skin preparation may be prepared into any one of formulations selected from the group consisting of cream, gel, patch, spray, ointment, plaster, lotion, liniment, paste, and cataplasma.

Additionally, the pharmaceutical composition may be used as a subcutaneous injection, and the subcutaneous injection may be injected subcutaneously using a conventional injection needle. Further, a direct injection into a region where hair growth is desired is also possible using a microneedle array in which a plurality of microneedles having a diameter of several tens to several hundred μm and a length of several tens to several thousand μm are arranged.

Another aspect of the present invention provides a cosmetic composition for promoting hair growth, or preventing or improving hair loss, comprising the compound of Chemical Formula 1 or a cosmetically acceptable salt thereof as an active ingredient.

As used herein, the term "cosmetically acceptable salt" is as defined in the term "pharmaceutically acceptable salt".

The cosmetic composition may be formulated into, for example, a hair tonic, a hair cream, a hair lotion, a hair shampoo, a hair rinse, a hair conditioner, a hair spray, a hair pack, a hair treatment, a soap, an eyebrow growth-promoting agent, an eyebrow nutrition agent, an eyelash growth-promoting agent, and an eyelash nutrition agent.

Additionally, the cosmetic composition may contain various ingredients that are blended in a conventional cosmetic composition, such as surfactants, vitamins, preservatives, thickeners, pH adjusters, flavoring agents, coloring agents, etc., depending on each formulation.

Still another aspect of the present invention provides a food composition for promoting hair growth, or preventing or improving hair loss, comprising the compound of Chemical Formula 1, or a sitologically acceptable salt thereof as an active ingredient.

As used herein, the term "sitologically acceptable salt" is as defined in the term "pharmaceutically acceptable salt".

The food composition of the present invention may be used as a health functional food. As used herein, the term "health functional food" refers to a food which is prepared and processed with raw materials or components having functionality useful for a human body. In particular, the term "functionality" refers to the intake intended for obtaining effects useful for health uses such as control of nutrients for the structure and function of the human body or physiological functions, etc.

The food composition of the present invention may comprise conventional food additives, and the conformity of the "food additive" is determined, as long as there are no other regulations, by way of a standard or criterion regarding the relevant article according to general provisions of the Korean Food Additives Codex and General Test Method approved by the Korean Food & Drug Administration.

Items listed in the "Korean Food Additives Codex" may include, for example, a chemical composite such as ketone, glycine, potassium citrate, nicotinic acid, cinnamic acid, etc., natural additives such as persimmon color, *Glycyrrhiza* extract, crystalline cellulose, Kaoliang color, guar gum, etc., and mixed preparations such as L-glutamic acid sodium agent, alkali agents for noodles, preservative formulation, tar color formulation, etc.

The food composition of the present invention may comprise a guanidine derivative or a sitologically acceptable salt thereof in an amount of 0.01% to 95% by weight, preferably 1% to 80% by weight, based on the total weight of the composition. In addition, the guanidine derivative or a sitologically acceptable salt thereof contained in the food composition of the present invention may be obtained by way of the same or similar method as the extraction method mentioned in the preparation of the pharmaceutical composition, but is not limited thereto.

Additionally, the food composition of the present invention can be prepared and processed in the form of tablets, capsules, powders, granules, liquids, pills, etc. for the purpose of promoting hair growth and/or improving hair loss.

For example, the health functional food in the form of a tablet may be prepared as follows: a mixture of the guanidine derivative or a sitologically acceptable salt, an excipient, a binder, and a disintegrant, etc., and other additives can be granulated using a conventional method, and then a compression molding process is performed with a lubricant. Alternatively, the mixture can be directly subjected to the compression molding process. In addition, the health functional food in the form of a tablet may include a sweetening agent, if necessary, and it can be coated with a coating material, if necessary.

In the case of a health functional food in the form of a capsule, a hard capsule can be prepared by filling a mixture of additives such as the guanine derivative or a sitologically acceptable salt thereof and an excipient, etc., or granules thereof or coated granules into a conventional hard capsule, and a soft capsule can be prepared by filling a mixture of additives such as the guanine derivative or a sitologically acceptable salt thereof and an excipient, etc. into a capsule base such as gelatin, etc. The soft capsule can contain a plasticizer such as glycerin or sorbitol, etc., a coloring agent, a preservative, etc., if necessary.

The health functional food in the form of a bolus can be prepared by molding a mixture of the guanine derivative or a sitologically acceptable salt thereof, an excipient, a binder, and a disintegrant, etc. by way of a suitable method, and can be coated with white sugar or other coating materials, or covered with starch, talc, or proper materials.

A health functional food in the form of a granule can be produced by granulating a mixture of the guanine derivative or a sitologically acceptable salt thereof, an excipient, a binder, and a disintegrant, etc. by way of a suitable method. When needed, it can include a flavoring agent, a sweetening agent, etc. When the health functional food in the form of a granule is subjected to a particle size test with No. 12 (1680 μm), No. 14 (1410 μm), and No. 45 (350 μm) sieves, all particles may pass through the No. 12 sieve, the residual amount may be no more than 5.0% with the No. 14 sieve, and the amount of particles passing through the No. 45 sieve may be no more than 15.0% based on the total amount thereof.

The definitions of terms such as the excipient, binder, disintegrant, lubricant, sweetening agent, flavoring agent, etc. are described in literature known in the art and may encompass those with the same or similar functions (*The Korean Pharmacopoeia Review*, Moonsungsa Publication Co., Korea Pharmaceutical University Association, 5$^{th}$ Ed., pp. 33-48, 1989).

There is no particular limitation on the types of the food, and examples of the food to which the extract of the present invention can be added may include beverages, gums, vitamin complexes, drink preparations, etc., and may also include all foods in the ordinary sense.

Even another aspect of the present invention provides a feed composition for promoting hair growth, or preventing or improving hair loss, comprising the compound of Chemical Formula 1, or a sitologically acceptable salt thereof as an active ingredient.

As used herein, the term "feed" refers to food ingested by an animal, and specifically, it may refer to a material that supplies organic or inorganic nutrients necessary to maintain the life of the animal or to produce meat, milk, etc. The feed may include feed additives and may be prepared in various forms known in the art.

The type of the feed is not particularly limited, and a feed conventionally used in the corresponding technical field may be used. Non-limiting examples of the feed include vegetable feeds such as grains, root plants, food processing by-products, algae, fibers, fat and oils, starches, meals, or grain by-products; and animal feeds such as proteins, inorganic substances, fat and oils, minerals, single-cell proteins, animal planktons, or foods. These feeds may be used alone or in a mixture of two or more thereof.

Additionally, the compound of the present invention or a sitologically acceptable salt thereof may be used as a feed additive added to a feed composition. The feed additive may be used to improve productivity or health of a target animal, but is not limited thereto. The feed additive may correspond to a supplementary feed under the Control of Livestock and Fish Feed Act.

The feed additive of the present invention may be used by further mixing one or more ingredients of organic acids such as citric acid, fumaric acid, adipic acid, lactic acid, etc. and natural antioxidants such as polyphenols, catechins, tocopherols, vitamin C, green tea extract, chitosan, tannic acid, etc., and depending on needs, other conventional additives such as buffers, bacteriostatic agents, etc. may be added. In addition, it may be formulated into a liquid, capsule, granule, or tablet as needed.

The feed or feed additive may further include substances exhibiting various effects such as supplementation of nutrients and prevention of weight loss, enhancement of digestive availability of fibers in the feed, improvement of oil quality, prevention of reproductive disorders and improvement in conception rates, prevention of high-temperature stress in summer, etc. For example, it may be used together with nutritional supplements, growth promoters, digestive absorption accelerators, and prophylactic agents, in addition to the main components such as various supplements such as amino acids, inorganic salts, vitamins, antioxidants, antifungal and microbial preparations, etc., vegetable protein feeds such as milled or crushed wheat, barley, corn, etc., animal protein feeds such as powdered blood, powdered meat, powdered fish, etc., animal fats, and vegetable fats.

The feed and feed additive of the present invention may be fed to a number of animals, including mammals and poultry. For example, in order to maintain or improve beauty, these can be used in livestock, such as cattle, goats, etc.; and pets such as dogs and cats, etc., but are not limited thereto.

Yet another aspect of the present invention provides a method for promoting hair growth, or preventing or treating hair loss, comprising administering the compound of Chemical Formula 1 or a pharmaceutically acceptable salt thereof as an active ingredient.

As used herein, the term "prevention" refers to all actions that suppress or delay the onset, spread, and recurrence of hair loss due to the administration of the composition of the present invention. In addition, the term "treatment" refers to all actions that alleviate or beneficially change the symptoms of the above disease by the administration of the composition of the present invention.

As used herein, the term "subject" refers to all animals including monkeys, cattle, horses, sheep, pigs, chickens, turkeys, quails, cats, dogs, mice, rats, rabbits, or guinea pigs, as well as humans having hair loss or at risk of having the same, and the disease may be effectively prevented or treated by administering the pharmaceutical composition of the present invention to the subject. The pharmaceutical composition of the present invention may be administered in combination with a conventional therapeutic agent.

As used herein, the term "administration" refers to the introduction of a predetermined substance to a patient by any appropriate method. The composition of the present invention may be administered via any common route as long as it can reach a desired tissue. The composition may be administered via an intraperitoneal route, an intravenous route, an intramuscular route, a subcutaneous route, an intradermal route, an oral route, a topical route, an intranasal route, an intrapulmonary route, or an intrarectal route, but is not limited thereto. In addition, the pharmaceutical composition of the present invention may be administered by any device capable of delivering an active component to the target cell.

Still further another aspect of the present invention provides the use of the compound of Chemical Formula 1, a pharmaceutically acceptable salt thereof, or a composition comprising the same as an active ingredient for promoting hair growth, or preventing or treating hair loss.

Still further another aspect of the present invention provides the use of the compound of Chemical Formula 1, a pharmaceutically acceptable salt thereof, or a composition comprising the same as an active ingredient for the manufacture of pharmaceuticals for promoting hair growth, or preventing or treating hair loss.

MODE FOR CARRYING OUT THE INVENTION

The present invention will be described in detail by way of Examples. However, these Examples are provided for illustrative purposes only, and the scope of the invention is not intended to be limited by these Examples.

Preparation of Reagents

As guanine derivatives, (N-1-(2-methyl)phenethylbiguanide (hereinafter referred to as "IM176OUT05" or "IM"), N-1-(3,4-dichloro)phenethylbiguanide (hereinafter, "IM176OUT04"), and 1-(3,4-dimethylphenethyl)guanide (hereinafter, "IM177OUT02") were synthesized. The synthesis was performed in the same manner as in Example 22, Example 1, and Example 133 of Korean Patent Laid-Open Publication No. 10-2016-0146852 (Dec. 21, 2016), respectively. In addition, minoxidil was purchased from Hyundai Pharm (Seoul, Republic of Korea), and metformin was purchased from Cayman Chemical (Ann Arbor, MI, USA). The chemical structural formulae of the guanidine derivatives of the present invention, minoxidil, and metformin are shown in FIG. 1.

Example 1. Reprogramming Effect of Guanine Derivatives

Example 1.1. Comparison of Reprogramming Effect of Guanine Derivatives in Mouse Cells Rotenone (ETC complex I inhibitor) was found to efficiently promote reprogramming of somatic cells at a subtoxic dose (10 nM), and thus, the effects of rotenone and the guanidine derivatives of the present invention on iPSC production were compared as follows (FIG. 2).

During reprogramming into iPSCs by introducing OSKM reprogramming factor into mouse embryonic fibroblasts (MEFs), rotenone, the guanidine derivatives of the present invention, and phenformin were treated at the indicated concentrations. After 14 days, alkaline phosphatase (AP) staining was performed (FIG. 2A), and the number of AP$^+$ colonies was quantified (FIG. 2b). As a result, IM156 and phenformin did not show an effect of promoting reprogramming, whereas the number of AP$^+$ colonies was increased by the treatment of IM176OUT05, IM176OUT04, and IM177OUT02. In particular, it was confirmed that when IM176OUT05 (hereinafter IM) was treated at concentrations of 10 nM, 20 nM, and 50 nM, it showed an effect of enhancing reprogramming with an efficiency of 16.8 times, 13.9 times, and 13.7 times, respectively. In the subsequent experiment, additional efficacy was evaluated using only the three compounds showing the effective reprogramming-enhancing effect.

Example 1.2. Confirmation of Reprogramming Effect of Guanine Derivatives in Human Cells During reprogramming into iPSCs by introducing OSKM reprogramming factor into human foreskin fibroblast (HFFs), rotenone, IM176OUT05, IM176OUT04, and IM177OUT02, which showed the reprogramming effect on the mice cells in Example 1.1, were treated at the indicated concentrations. After 28 days, AP staining was performed (FIG. 3a), and the number of AP$^+$ colonies was quantified (FIG. 3b). As a result, all three compounds showed the most excellent reprogramming efficacy when treated at the 10 nM concentration. In particular, when IM176OUT05 was treated at 10 nM, 100 nM, and 500 nM concentrations, it showed an effect of enhancing reprogramming with an efficiency of 2.4 times or more.

Example 1.3. Confirmation of Effect of Maintaining Stemness of Guanidine Derivatives Additionally, the effect of the compounds of the present invention on maintaining sternness of human embryonic stem cells (hESCs) was confirmed (FIG. 4). Specifically, when hESCs were cultured in an unconditioned medium (UM), the sternness was lost, and AP activity was weakened (FIG. 4a). In contrast, when treated with IM176OUT05, IM176OUT04, and IM177OUT02, an increase in AP staining was observed at a low dose. In particular, when IM176OUT05 was treated at 10 nM and 100 nM concentrations, it was confirmed that the effect of maintaining the stemness was improved by 7.6 times and 8.2 times, respectively (FIG. 4b).

From the results of Examples 1.1 to 1.3, it was confirmed that IM176OUT05 at a concentration of 10 nM most efficiently enhanced the reprogramming effect in the process of producing mouse and human iPSCs, and also exhibited the efficacy of maintaining stemness of human embryonic stem cells. Thus, in the following examples, a follow-up study was performed using the above conditions.

Example 2. Test of Hair Regeneration Effect of IM176OUT05

Example 2.1. Hair Regeneration Model

During the hair telogen phase, the hair on the dorsal skin of 7-week-old C57BL/6 mice (Dae Han BioLink, Chungbuk, Republic of Korea) was depilated using an animal clipper and wax (Veet, Oxy Reckitt Benckiser, Seoul, Republic of Korea). From the next day, 200 μL of placebo (control), 1% IM, 1% minoxidil, or 1% metformin was applied daily to the depilated area using a sterile cotton swab. Images of each animal were captured daily, and the degree of darkness of the color on dorsal skin was quantified in the same area (1.6 cm×3 cm) using the Image J program. The mice were sacrificed, and skin tissues on days 0, 7, 14, and 20 were obtained. Half of the tissues were used for RNA isolation, and the other half were fixed with 4% paraformaldehyde overnight for histochemical analysis.

Example 2.2. Histochemical Analysis

The tissues fixed in Example 1.1. were immersed in 30% sucrose, and then embedded in an OCT compound (Sakura Finetek USA Inc, Torrance, CA, USA). Frozen fragments were obtained using a cryostat sectioning device (Leica, Wetzlar, Germany) and stained using hematoxylin (Sigma) and eosin (Sigma) (H&E), or each of the antibodies shown in Table 1 below. Immunohistochemical analysis was performed, and fluorescence images were taken with an Olympus microscope (Olympus)

TABLE 1

| Antibodies | Catalogue No. | Name of Company | Dilution Rate |
|---|---|---|---|
| anti-Cytokeratin 15 | ab52816 | abcam | 1:100 |
| anti-β-catenine c | ab32572 | abcam | 1:200 |
| anti-β-catenine (FACS) | ab22656 | abcam | 1:500 |
| anti-Ki67 | ab15580 | abcam | 1:200 |
| anti-shh (IHC) | sc-9024 | Santacruz | 1:80 |
| anti-shh (FACS) | ab135240 | abcam | 1:300 |
| anti-PDK | sc-7140 | Santacruz | 1:50 |
| anti-PDH (rabbit IgG) | sc-292543 | Santacruz | 1:50 |
| anti-PDH (mouse IgG) | sc-377092 | Santacruz | 1:50 |
| Normal Rabbit IgG | #2729 | Cell signaling technology | 1:500 |
| anti-Histon H3 | #4620 | Cell signaling technology | 1:50 |
| anti-trimethyl-Histone H3 (Lys4) | 04-745 | Millipore | 1:200 |
| anti- trimethyl-Histone H3 (Lys27) | 07-449 | Millipore | 1:200 |
| anti-dimethyl-Histone H3 (Lys9) | 07-441 | Millipore | 1:200 |
| anti-NANOG | A300-397A | Bethyl Lab | 1:250 |
| anti-SSEA1 | MAB2155 | R&D Systems | 1:200 |

Example 2.3. Quantitative Histomorphometric Analysis

According to the guidelines for accurately classifying the hair cycle stages, the hair cycle was quantified by classifying individual hair follicles with H&E staining micrographs in the longitudinal section of each mouse (n>10). The percentage of the anagen phase of the hair was calculated for each group. Hair follicles in the same area (1300 μm width) were counted by H&E staining micrographs in the cross section of each mouse (n>10).

Example 2.4. FACS Analysis

After the mice were perfused with PBS to remove blood, the skin tissue was harvested and cut into small pieces. The tissue was digested with trypsin (Thermo Fisher Scientific) at 37° C. for 150 minutes, then filtered through a 75 μm nylon mesh, followed by filtering through a 30 μm mesh (BD Biosciences). Single cells were fixed, permeabilized, and blocked according to the immunostaining protocol. The cells were stained with specific antibodies (Table 1 above) and analyzed with BD Accuri™ C6 (BD Biosciences)

Example 2.5. Auricle Punch Analysis

For the auricular tissue repair analysis, three holes with a diameter of 2 mm were drilled in each ear using a punching instrument (Fine Science Tools, British Columbia, Canada). IM at the indicated concentration was applied daily with a sterile cotton swab. The hole area was measured with digital calipers (VWR, Radnor, PA, USA).

Statistical Analysis

All figures are representative of three or more independent biological data repeatedly tested. All animal experiments were independently repeated 6 times in the treatment group of n>5. Student's t-test is used for comparison between groups; p<0.05 indicates statistical significance.

Example 3. Confirmation of Hair Regeneration Effect of IM176OUT05

Example 3.1. Effect of IM176OUT05 on Promoting Hair Growth in Mice

It was confirmed whether the IM compound can promote hair growth without showing toxicity or other side effects through mouse experiments. In 7-week-old C57BL/6 mice, the telogen phase was motivated by hair removal, and various concentrations of IM were applied topically to the dorsal skin of the mice daily. On day 9, black pigmentation and hair growth were remarkably observed in the area to which 1% IM was applied.

Additionally, as a result of comparing the efficacy of IM and minoxidil, a conventional hair growth promoter, it was confirmed that IM promoted hair growth in both male and female mice. In particular, IM showed a strong promoting effect on hair growth in female mice. Specifically, on day 8 of IM treatment, it was confirmed that the skin color was clearly darkened in the IM-treated mice compared to the control or minoxidil-treated mice. In addition, on day 10, the hair growth was markedly promoted by IM treatment (FIG. 5). Separately, as a result of additionally performing an independent experiment, it was confirmed that IM exhibited an excellent effect as compared to minoxidil in female mice (FIG. 10). In contrast, it was found that the effect of IM was similar to that of minoxidil in male mice (FIGS. 11a and 11b).

In addition, as a result of comparing the effects of IM and metformin, another biguanide derivative, for hair growth, the darkness intensity on the dorsal skin of the metformin-treated mice slightly was increased compared to the control group from day 8, but did not show a remarkable effect (FIGS. 13a and 13b).

No side effects, including skin problems, were observed in the IM-treated mice during the experiment.

Example 3.2. Effects of IM176OUT05 on Promoting Hair Follicle Regeneration in Mice As a result of analyzing the tissues through histomorphometry, it was confirmed that IM stimulated the progression of the hair follicle cycle (FIG. 6a). On day 20, in the longitudinal section, most of the hair follicles in the control mice appeared quantitatively in growth phase III, whereas in the IM-treated mice, it was confirmed that most of the hair follicles appeared mainly in growth phases V and VI, which are the later stages of the growth phase (FIG. 6b). Additionally, on day 7, in the cross section, the number of hair follicles was significantly increased in the IM-treated mice compared to the control group (FIG. 6c), and the number of hair follicles in the IM-treated mice or minoxidil-treated mice was significantly higher than that of the control group on day 20 (FIG. 6d). Moreover, on day 7, keratin 15 (K15), a marker of hair follicle stem cells, was strongly expressed in the follicle protrusion region of the IM-treated mice compared to the control or minoxidil-treated mice (FIG. 7a).

Further, on day 7, the expression of R-catenin, which mediates hair follicle regeneration, was increased in the IM-treated mice. In particular, Ki67-positive proliferating cells were identified in the IM-treated mice, indicating that the hair follicle cycle and additional expansion of proliferative progenitor cells were increased by IM (FIG. 7a). As a result of quantifying the $K15^+/\beta\text{-catenin}^+$ population by FACS analysis, the $K15^+/\beta\text{-catenin}^+$ population occupied the cell population by 3.2%, 11.7%, and 6.0% in the single skin cells of the control, IM-treated mice, and minoxidil-treated mice, respectively (FIG. 7b). The results indicate that the cell population was increased by 3.7 in the IM-treated mice as compared to the control group (FIG. 7b).

Until day 20, the K15 and β-catenin were strongly detected in all mouse groups (FIG. 7c), and the $K15^+/\beta\text{-catenin}^+$ population was detected in an amount of 24% or more in all groups (FIG. 7d). Sonic hedgehog (Shh), another essential factor for hair follicle development, was clearly detected in the IM-treated mice or minoxidil-treated mice (FIG. 7c). On day 7, the $Ki67^+/Shh^+$ population was detected in an amount of less than 5% in all mouse groups (FIG. 7b), but on day 20, it increased to 13.8%, 36.7%, and 34% in the single skin cells of the control, IM-treated, and minoxidil-treated mice, respectively (FIG. 7d). On day 20, the $Ki67^+/Shh^+$ population was increased by 2.7 times in the IM-treated mice as compared to the control group (FIG. 7d).

Example 3.3. Effects of IM176OUT05 on Stem Cell Metabolism and Proliferation Activity of Proliferative Progenitor Cells in Early Stage of Hair Follicle Regeneration It is known that K15-positive hair follicle stem cells express pyruvate dehydrogenase kinase (PDK), an enzyme that promotes the conversion to glycolysis, whereas Ki67-positive proliferating cells strongly express pyruvate dehydrogenase (PDH), an enzyme that responds to mitochondrial OXPHOS. On day 7, PDK expression was detected in the K15-positive stem cells of the IM-treated mice, but was not detected in the control or minoxidil-treated mice (FIG. 8a). As a result of performing FACS analysis on day 7, it was confirmed that the $K15^+/PDK^+$ population was not detected in the control or minoxidil-treated mice, but occupied the cell population by 5.9% in the single skin cells of the IM-treated mice (FIG. 8c). Through this finding, it was confirmed that the glycolytic stem cell population ($K15^+/PDK^+$) was increased by at least 6.6 times or more in the IM-treated mice as compared to the control group.

On day 7, PDH expression was clearly confirmed in the Ki67-positive proliferating cells of the IM-treated mice (FIG. 8a), and the expression was detected at a very high level in the proliferating cells of all groups on day 20 (FIG. 8b). In addition, on day 7, the $Ki67^+/PDH^+$ population showed an increase of 13.7% in the IM-treated mice, while showing decreases of 5.0% and 8.3% in the control and minoxidil-treated mice, respectively (FIG. 8c). Subsequently, as a result of analyzing the mutual expression pattern of each marker, the K15/PDH and Ki67/PDK expressions were independently detected in the IM-treated mice on day 20 (FIG. 12a). This indicates that PDK-expressing glycolytic K15-positive hair follicle stem cells and PDH-expressing OXPHOS-dependent Ki67-positive proliferating cells were clearly distinguished from each other. Moreover, through FACS analysis, the PDK+ cell population and the Ki67+ cell population were clearly separated, and it was confirmed that each population was increased by the IM-treatment or minoxidil-treatment on day 20 (FIG. 12b). The separated populations of PDH+ cells and K15+ cells, which were increased by IM treatment or minoxidil treatment, were also detected on day 20 (FIG. 12b).

Example 3.4. Effect of Expression of Genes Related to Metabolism and Hair Regeneration Due to IM176OUT05

The level of expression of genes related to metabolism and hair regeneration was analyzed through the skin tissue of each mouse group. The expression of glycolysis-related enzymes (HK2 and LDHA) was significantly induced in the IM-treated mice on day 7, and was significantly increased in both the IM-treated and minoxidil-treated mice on day 20 compared to the control. At this stage, the expression of OXPHOS-related enzymes (NDUS3 and ATP5B) was increased in both the IM-treated and minoxidil-treated mice compared to the control. This suggests that IM can promote glycolysis in the early stages of hair follicle regeneration, further promoting OXPHOS in later stages, and thereby contributing to the active energy metabolism required for hair growth. The expression of stemness-related genes (Wnt1a, Lef-1, Gli-1, and versican) involved in the hair follicle development was significantly upregulated in the skin of the IM-treated mice on day 7, and the expression of Wnt1a, Lef-1, and Gli-1 was slightly increased in the minoxidil-treated mice as compared to the control. On day 20, the stemness-related genes were significantly induced in both the IM-treated mice and minoxidil-treated mice as compared to the control group (FIG. 8d).

Example 3.5. Tissue Regeneration Effect Due to IM176OUT05

The effect of IM on tissue regeneration was observed through auricular tissue repair. As a result, it was confirmed that IM reduced the wound area of the auricle in a dose-dependent manner. This suggests that IM can activate tissue regeneration in addition to hair growth (FIG. 14). Based on these results, IM can repair hair follicle tissue damaged by hair loss and prevent possible damage in advance.

Those of ordinary skill in the art will recognize that the present invention may be embodied in other specific forms without departing from the spirit or essential characteristics thereof. The described embodiments are to be considered in all respects only as illustrative and not restrictive. The scope of the present invention is therefore indicated by the appended claims rather than by the foregoing description. All changes which come within the meaning and range of equivalency of the claims are to be embraced within the scope of the present invention.

The invention claimed is:

1. A method for regenerating tissue, promoting hair growth, or preventing or treating hair loss in a subject in need thereof, comprising administering a pharmaceutical composition comprising any one of compounds of Chemical Formula 2 to 4 below, or a pharmaceutically acceptable salt thereof, as an active ingredient:

[Chemical Formula 2]
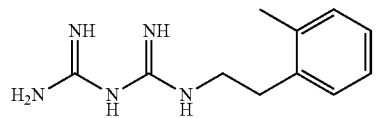

[Chemical Formula 3]
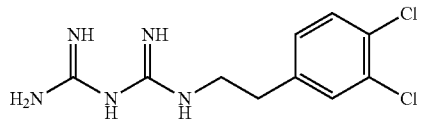

[Chemical Formula 4]
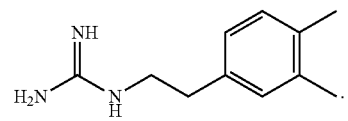

wherein the composition promotes glycolysis in the early stages of hair follicle regeneration.

2. The method of claim 1, wherein the composition comprises any one of compounds of Chemical Formula 2 to 4, or a pharmaceutically acceptable salt thereof in a concentration of 1 to 5%.

3. The method of claim 1, wherein the composition is formulated into a preparation for external application to skin.

4. The method of claim 3, wherein the preparation is any one selected from the group consisting of cream, gel, patch, spray, ointment, plaster, lotion, liniment, paste, and cataplasma.

5. A method for regenerating tissue, promoting hair growth, or preventing or improving hair loss in a subject in need thereof, comprising administering a cosmetic composition comprising any one of compounds of Chemical Formula 2 to 4 below, or a cosmetically acceptable salt thereof, as an active ingredient:

[Chemical Formula 2]
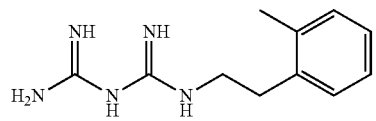

[Chemical Formula 3]
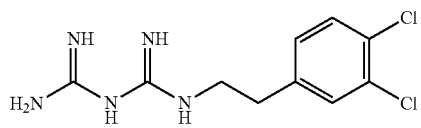

[Chemical Formula 4]
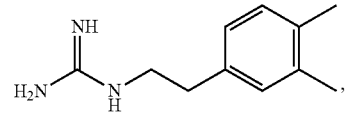

wherein the composition promotes glycolysis in the early stages of hair follicle regeneration.

6. The method of claim 5, wherein the tissue is a hair follicle or skin.

7. A method for regenerating tissue, promoting hair growth, or preventing or improving hair loss in a subject in need thereof, comprising administering a food composition comprising any one of compounds of Chemical Formula 2 to 4 below, or a sitologically acceptable salt thereof, as an active ingredient:

[Chemical Formula 2]

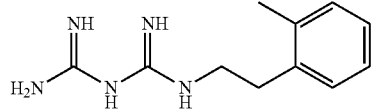

[Chemical Formula 3]

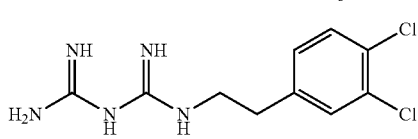

[Chemical Formula 4]

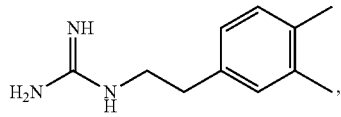

, wherein the composition promotes glycolysis in the early stages of hair follicle regeneration.

8. The method of claim 7, wherein the tissue is a hair follicle or skin.

9. The method of claim 1, wherein the tissue is a hair follicle or skin.

* * * * *